US009511144B2

(12) United States Patent
Jones et al.

(10) Patent No.: US 9,511,144 B2
(45) Date of Patent: Dec. 6, 2016

(54) COSMETIC COMPOSITIONS AND METHODS PROVIDING ENHANCED PENETRATION OF SKIN CARE ACTIVES

(71) Applicant: The Procter & Gamble Company, Cincinnati, OH (US)

(72) Inventors: Stevan David Jones, Singapore (SG); Kunal Virendra Gujraty, Bangalore (IN); Naohisa Yoshimi, Singapore (SG); Monalisha Paul, Kolkata (IN); James Terence Wescott, Portishead (GB)

(73) Assignee: The Procter & Gamble Company, Cincinnati, OH (US)

( * ) Notice: Subject to any disclaimer, the term of this patent is extended or adjusted under 35 U.S.C. 154(b) by 225 days.

(21) Appl. No.: 13/803,692

(22) Filed: Mar. 14, 2013

(65) Prior Publication Data

US 2014/0275184 A1 Sep. 18, 2014

(51) Int. Cl.
| | |
|---|---|
| *A61K 47/10* | (2006.01) |
| *A61K 31/455* | (2006.01) |
| *A61Q 19/00* | (2006.01) |
| *A61K 8/34* | (2006.01) |
| *A61K 8/67* | (2006.01) |

(52) U.S. Cl.
CPC ............. *A61K 47/10* (2013.01); *A61K 8/342* (2013.01); *A61K 8/345* (2013.01); *A61K 8/675* (2013.01); *A61K 31/455* (2013.01); *A61Q 19/00* (2013.01)

(58) Field of Classification Search
CPC ...... A61K 31/455; A61K 47/10; A61K 8/342; A61K 8/345; A61K 8/673; A61K 8/675; A61Q 17/00; A61Q 19/00
See application file for complete search history.

(56) References Cited

U.S. PATENT DOCUMENTS

| | | |
|---|---|---|
| 3,755,560 A | 8/1973 | Dickert et al. |
| 4,421,769 A | 12/1983 | Dixon et al. |
| 4,781,917 A | 11/1988 | Luebbe et al. |
| 4,859,653 A | 8/1989 | Morelle et al. |
| 4,970,252 A | 11/1990 | Sakuta et al. |
| 5,211,950 A | 5/1993 | Kobayashi et al. |
| 5,229,104 A | 7/1993 | Sottery et al. |
| 5,254,338 A | 10/1993 | Sakai et al. |
| 5,413,781 A | 5/1995 | Giwa-Agbomeirele et al. |
| 5,550,166 A | 8/1996 | Ostlund et al. |
| 5,569,464 A | 10/1996 | Endo et al. |
| 5,654,362 A | 8/1997 | Schulz, Jr. et al. |
| 5,686,082 A | 11/1997 | N'Guyen |
| D391,162 S | 2/1998 | Kokenge |
| 5,725,845 A | 3/1998 | Krog et al. |
| 5,760,116 A | 6/1998 | Kilgour et al. |
| 5,833,998 A | 11/1998 | Biedermann et al. |
| 5,906,979 A | 5/1999 | Allan |
| 5,939,082 A | 8/1999 | Oblong et al. |
| 5,958,386 A | 9/1999 | Sawin et al. |
| 5,980,921 A | 11/1999 | Biedermann et al. |
| 6,010,708 A | 1/2000 | Ogihara et al. |
| 6,015,568 A | 1/2000 | Segot et al. |
| 6,086,918 A | 7/2000 | Stern et al. |
| 6,159,485 A | 12/2000 | Yu et al. |
| 6,174,533 B1 | 1/2001 | SaNogueira |
| 6,217,888 B1 | 4/2001 | Oblong et al. |
| 6,238,678 B1 | 5/2001 | Oblong et al. |
| 6,245,342 B1 | 6/2001 | Golz-Berner et al. |
| 6,274,151 B1 | 8/2001 | Michel et al. |
| 6,296,859 B1 | 10/2001 | Stoltz |
| 6,391,863 B1 | 5/2002 | Philippe et al. |
| 6,440,435 B1 | 8/2002 | Michel et al. |
| 6,524,593 B1 | 2/2003 | Yu et al. |
| 6,563,012 B2 | 5/2003 | Hill |
| 6,669,932 B2 | 12/2003 | Imanaka et al. |
| 6,746,765 B1 | 6/2004 | Fattman |
| 6,790,435 B1 | 9/2004 | Ma et al. |
| 6,872,401 B2 | 3/2005 | Seyler et al. |
| 6,881,726 B2 | 4/2005 | Chang et al. |
| 6,939,537 B2 | 9/2005 | Ohta et al. |
| D516,436 S | 3/2006 | Campbell et al. |
| 7,054,674 B2 | 5/2006 | Cane et al. |
| 7,083,780 B2 | 8/2006 | Ansmann et al. |
| 7,094,842 B2 | 8/2006 | Lennon |
| D535,191 S | 1/2007 | Corker |

(Continued)

FOREIGN PATENT DOCUMENTS

| | | |
|---|---|---|
| CN | 1762967 | 4/2006 |
| CN | 101366698 A | 2/2009 |

(Continued)

OTHER PUBLICATIONS

Derwent Abstract of EP 2253305 A2; Derwent-Acc-No: 2010-P41087; Orginal Publication Date: Nov. 24, 2010.*
Sepiwhite MSH. Research Disclosure. Mason Publications Hampshire. GB. vol. 462, No. 21. Oct. 1, 2002 (Oct. 1, 2002).
Bissett Donald L et al: "Reduction in the appearance of facial hyperpigmentation by topical N-undecyl-10-enoyl-L-phenylalanine and its combination with niacinamide", Journal of Cosmetic Dermatology. Blackwell Science, Oxford. GB, vol. 8, No. 4. Dec. 1, 2009 (Dec. 1, 2009), pp. 260-266.
Mintel Database Oct. 2010 (Oct. 2010). "Cellular Total Eye Care" La Colline Cellulary Research Laboratories, 6 pages http://www.gnpd.com.
Mintel Database May 2008 (May 2008). "Color Repair Tinted Moisturizing Anti-Wrinkle Cream" Institut Esthederm, 3 pages http://www.gnpd.com.

(Continued)

*Primary Examiner* — Sreeni Padmanabhan
*Assistant Examiner* — Jody Karol
(74) *Attorney, Agent, or Firm* — Betty J. Zea

(57) ABSTRACT

A cosmetic composition suitable for topical application is provided. In some examples, the cosmetic composition can include glycerin, hexyldecanol, a vitamin B compound, and one or more materials selected from the group consisting of 1,2-pentanediol, 1,4-pentanediol, 2,4-pentanediol, 1,5-pentanediol, 1,2-butanediol, 1,3-butanediol, 1,4-butanediol, 2,3-butanediol, 1,2-hexanediol, 1,5-hexanediol, 1,6-hexanediol, 2,5-hexanediol, hexylene glycol, and combinations thereof.

7 Claims, 7 Drawing Sheets

(56) References Cited

U.S. PATENT DOCUMENTS

| | | |
|---|---|---|
| 7,179,880 B2 | 2/2007 | Kawa et al. |
| D542,660 S | 5/2007 | Thomas et al. |
| D547,193 S | 7/2007 | Blasko et al. |
| D547,661 S | 7/2007 | Blasko et al. |
| 7,255,704 B2 | 8/2007 | Hogan et al. |
| 7,285,570 B2 | 10/2007 | Robinson et al. |
| 7,297,668 B2 | 11/2007 | Johansson et al. |
| D558,591 S | 1/2008 | Blasko et al. |
| D563,221 S | 3/2008 | Ashiwa et al. |
| 7,347,990 B2 | 3/2008 | Emslie et al. |
| D570,707 S | 6/2008 | Blasko et al. |
| 7,488,841 B2 | 2/2009 | Yamawaki et al. |
| 7,572,435 B2 | 8/2009 | Kawa et al. |
| 7,811,342 B1 | 10/2010 | Hsu |
| 7,850,955 B2 | 12/2010 | Saito et al. |
| 7,871,635 B2 | 1/2011 | Stolz et al. |
| 7,883,691 B2 | 2/2011 | Kalejman |
| 7,947,097 B2 | 5/2011 | You |
| 7,968,607 B2 | 6/2011 | Nishijima et al. |
| 7,970,456 B2 | 6/2011 | Preece et al. |
| 7,993,420 B2 | 8/2011 | Haerle et al. |
| 8,038,751 B2 | 10/2011 | Starling |
| 8,062,394 B2 | 11/2011 | Gaeta et al. |
| 8,063,097 B2 | 11/2011 | Robinson et al. |
| 8,080,586 B2 | 12/2011 | Kawa et al. |
| 8,101,574 B2 | 1/2012 | Gillon et al. |
| 8,298,572 B2 | 10/2012 | Iwao et al. |
| 8,398,964 B2 | 3/2013 | Kamei et al. |
| 8,399,415 B2 | 3/2013 | Gillon et al. |
| 8,420,853 B2 | 4/2013 | Cho et al. |
| 8,507,649 B2 | 8/2013 | Lintner et al. |
| 8,524,204 B2 | 9/2013 | Hakozaki et al. |
| 8,715,628 B1 | 5/2014 | Hakozaki et al. |
| 8,871,717 B2 | 10/2014 | Osborne |
| 8,940,943 B2 | 1/2015 | Beckedahl et al. |
| 8,956,598 B2 | 2/2015 | Jackwerth et al. |
| 8,968,712 B2 | 3/2015 | Tanaka |
| 9,090,755 B2 | 7/2015 | Nakahishi et al. |
| 2001/0002257 A1 | 5/2001 | Stolz |
| 2002/0006906 A1 | 1/2002 | Stoltz et al. |
| 2002/0041889 A1 | 4/2002 | Masuda et al. |
| 2002/0182237 A1 | 12/2002 | Bissett et al. |
| 2002/0192169 A1 | 12/2002 | Chevalier et al. |
| 2003/0059447 A1 | 3/2003 | Lambers |
| 2003/0091620 A1 | 5/2003 | Fikstad et al. |
| 2003/0134780 A1 | 7/2003 | Patt |
| 2003/0198656 A1 | 10/2003 | Yu et al. |
| 2003/0229141 A1 | 12/2003 | Yu et al. |
| 2004/0009140 A1 | 1/2004 | Nishijima et al. |
| 2004/0044078 A1 | 3/2004 | Kawa et al. |
| 2004/0091493 A1 | 5/2004 | Perrier et al. |
| 2004/0142853 A1 | 7/2004 | Patt |
| 2004/0170586 A1 | 9/2004 | Ferrari et al. |
| 2004/0175347 A1 | 9/2004 | Bissett |
| 2005/0002894 A1 | 1/2005 | Petersohn et al. |
| 2005/0013784 A1 | 1/2005 | Trigg et al. |
| 2005/0019356 A1 | 1/2005 | Bissett |
| 2005/0079141 A1 | 4/2005 | Zander et al. |
| 2005/0106190 A1 | 5/2005 | Kawa et al. |
| 2005/0112156 A1 | 5/2005 | Busch et al. |
| 2005/0118119 A1 | 6/2005 | Stoltz |
| 2005/0249689 A1 | 11/2005 | Kuo et al. |
| 2005/0249690 A1 | 11/2005 | Rojas-Wahl et al. |
| 2006/0045890 A1 | 3/2006 | Gonzalez et al. |
| 2006/0089553 A1 | 4/2006 | Cotton |
| 2006/0216254 A1 | 9/2006 | Majmudar et al. |
| 2006/0263309 A1 | 11/2006 | Bissett |
| 2006/0275218 A1* | 12/2006 | Tamarkin et al. ............. 424/45 |
| 2006/0275237 A1 | 12/2006 | Bissett et al. |
| 2006/0280711 A1 | 12/2006 | Cornell et al. |
| 2007/0028089 A1 | 2/2007 | Yukawa et al. |
| 2007/0040306 A1 | 2/2007 | Morel et al. |
| 2007/0135379 A1 | 6/2007 | Mallard et al. |
| 2007/0172436 A1 | 7/2007 | Zhang |
| 2007/0185038 A1 | 8/2007 | Bissett et al. |
| 2007/0203240 A1 | 8/2007 | Oblong et al. |
| 2007/0205226 A1 | 9/2007 | Honda et al. |
| 2007/0264224 A1 | 11/2007 | Morris et al. |
| 2007/0270472 A1 | 11/2007 | Beumer et al. |
| 2007/0281033 A1 | 12/2007 | Rochat |
| 2007/0292358 A1 | 12/2007 | Emmerling et al. |
| 2007/0297996 A1 | 12/2007 | Tanner |
| 2008/0057015 A1 | 3/2008 | Oblong et al. |
| 2008/0059313 A1 | 3/2008 | Oblong et al. |
| 2008/0081052 A1 | 4/2008 | Zhang |
| 2008/0152604 A1 | 6/2008 | Doering et al. |
| 2008/0154030 A1 | 6/2008 | Chang et al. |
| 2008/0169215 A1 | 7/2008 | Tanaka et al. |
| 2008/0206373 A1 | 8/2008 | Millikin et al. |
| 2008/0207771 A1 | 8/2008 | Dikstein |
| 2008/0233183 A1 | 9/2008 | McCook |
| 2008/0241088 A1 | 10/2008 | Joshi et al. |
| 2008/0269352 A1 | 10/2008 | Falkowski et al. |
| 2008/0305059 A1 | 12/2008 | Chaudhuri |
| 2008/0312304 A1 | 12/2008 | Zhang |
| 2009/0017080 A1 | 1/2009 | Tanner et al. |
| 2009/0093388 A1 | 4/2009 | Yamawaki et al. |
| 2009/0098173 A1 | 4/2009 | Robinson et al. |
| 2009/0124693 A1 | 5/2009 | Beumer |
| 2009/0162443 A1 | 6/2009 | Anthony et al. |
| 2009/0238877 A1 | 9/2009 | Suda et al. |
| 2009/0317345 A1 | 12/2009 | Joshi et al. |
| 2010/0183527 A1 | 7/2010 | Moser et al. |
| 2010/0186669 A1 | 7/2010 | Shin et al. |
| 2010/0189669 A1 | 7/2010 | Hakozaki |
| 2010/0189754 A1 | 7/2010 | Yoshida et al. |
| 2010/0249043 A1 | 9/2010 | Lin |
| 2010/0286102 A1 | 11/2010 | Vielhaber |
| 2010/0305169 A1 | 12/2010 | Robinson et al. |
| 2011/0059032 A1 | 3/2011 | Dierker et al. |
| 2011/0091404 A1 | 4/2011 | Wöhrle et al. |
| 2011/0097286 A1 | 4/2011 | Swanson et al. |
| 2011/0097391 A1 | 4/2011 | Grigor'ev et al. |
| 2011/0104089 A1 | 5/2011 | Wöhrle et al. |
| 2011/0110874 A1 | 5/2011 | Tanaka et al. |
| 2011/0162287 A1 | 7/2011 | Cai |
| 2011/0305657 A1 | 12/2011 | Kuper et al. |
| 2012/0082717 A1 | 4/2012 | Char et al. |
| 2012/0128603 A1* | 5/2012 | Tanaka ........................... 424/59 |
| 2012/0148510 A1 | 6/2012 | Hakozaki |
| 2012/0148515 A1 | 6/2012 | Hakozaki |
| 2012/0156146 A1 | 6/2012 | Hakozaki |
| 2012/0189678 A1 | 7/2012 | Li et al. |
| 2013/0274762 A1 | 10/2013 | Guay et al. |
| 2014/0328774 A1 | 11/2014 | Rout et al. |
| 2015/0139923 A1 | 5/2015 | Tanaka |

FOREIGN PATENT DOCUMENTS

| | | |
|---|---|---|
| DE | 199 28 112 A1 | 12/2000 |
| DE | 10 2005 063 062 A1 | 7/2007 |
| DE | 10 2006 058 611 A1 | 6/2008 |
| DE | 10 2007 059 679 A1 | 9/2008 |
| DE | 10 2008 012 457 A1 | 12/2008 |
| DE | 10 2008 031 556 A1 | 4/2009 |
| DE | 10 2008 052 053 A1 | 5/2009 |
| DE | 10 2008 052 054 A1 | 5/2009 |
| DE | 10 2008 052 521 A1 | 5/2009 |
| DE | 10 2008 047 944 A1 | 6/2009 |
| DE | 10 2008 047 945 A1 | 6/2009 |
| DE | 10 2008 053 271 A1 | 4/2010 |
| DE | 10 2008 053 273 A1 | 4/2010 |
| DE | 10 2009 034 140 A1 | 5/2010 |
| DE | 10 2009 050 430 A1 | 6/2010 |
| EP | 0328099 A1 | 8/1989 |
| EP | 0415598 A1 | 3/1991 |
| EP | 1046393 A1 | 10/2000 |
| EP | 1083257 A1 | 3/2001 |
| EP | 1083261 A1 | 3/2001 |
| EP | 1 634 576 A1 | 3/2006 |
| EP | 1 640 041 A2 | 3/2006 |
| EP | 1 521 586 B1 | 4/2007 |
| EP | 1 790 330 A2 | 5/2007 |
| EP | 1 803 435 A2 | 7/2007 |

(56) References Cited

FOREIGN PATENT DOCUMENTS

| | | |
|---|---|---|
| EP | 1 815 843 A2 | 8/2007 |
| EP | 1 964 540 A2 | 9/2008 |
| EP | 1 994 923 A2 | 11/2008 |
| EP | 2 116 221 A1 | 11/2009 |
| EP | 2 253 305 A2 | 11/2010 |
| EP | 2253305 A2 * | 11/2010 |
| FR | 2702959 A1 | 9/1994 |
| FR | 2765105 A1 | 12/1998 |
| FR | 2771632 A1 | 6/1999 |
| FR | 2 859 104 A1 | 3/2005 |
| FR | 2 863 893 B1 | 4/2008 |
| FR | 2913598 | 9/2008 |
| FR | 2 913 598 B1 | 10/2009 |
| JP | 46014357 A | 4/1971 |
| JP | 47014342 A | 8/1972 |
| JP | 61229812 A | 10/1986 |
| JP | AS62042733 | 2/1987 |
| JP | 6118708 A | 4/1994 |
| JP | 73312281 A | 12/1995 |
| JP | 11021582 A | 1/1999 |
| JP | 2006016401 | 1/2006 |
| JP | A2006137684 | 6/2006 |
| KR | 9616193 B1 | 12/1996 |
| WO | WO 97/17060 A1 | 5/1997 |
| WO | WO 97/39733 A1 | 10/1997 |
| WO | WO 97/39734 A1 | 10/1997 |
| WO | WO 98/09611 A1 | 3/1998 |
| WO | WO 99/04757 A1 | 2/1999 |
| WO | WO 99/27902 A | 6/1999 |
| WO | WO 00/40217 A1 | 7/2000 |
| WO | WO 01/01962 | 1/2001 |
| WO | WO 02/062312 A1 | 8/2002 |
| WO | WO 03/061768 A2 | 7/2003 |
| WO | WO 2004/000248 A2 | 12/2003 |
| WO | WO 2008/101693 A2 | 8/2008 |
| WO | WO 2009/105294 | 8/2009 |

OTHER PUBLICATIONS

Mintel Database Oct. 2011 (Oct. 2011). "Dark Spot Corrector" Philosophy, 5 pages http://www.gnpd.com.
Mintel Database Feb. 2005 (Feb. 2005). "Extreme Bronz Repair Tanning Cream" Mary Cohr, 5 pages http://www.gnpd.com.
Mintel Database Nov. 2011 (Nov. 2011). "Serum" Institut Esthederm, 2 pages http://www.gnpd.com.
Mintel Database Oct. 2003 (Oct 2003). "Supertanning Moisturising Mild Spray SPF 15" Collistar, 3 pages http://www.gnpd.com.
Mintel Database Oct. 2003 (Oct. 2003). "Virtual Youth Lifting Moisture Makeup (35)" Prescriptives 2 pages http://www.gnpd.com.
Mintel Database Dec. 2009 (Dec. 2009). "White Crystal BB Cream SPF 35/PA++" The Face Shop, 3 pages http://www.gnpd.com.
International Search Report; PCT/CN2011/000111; International Filing Date Jan. 25, 2011; 12 pages.
All Office Actions, U.S. Appl. No. 13/299,042.
All Office Actions, U.S. Patent Application No. 13/299,051.
Marjukka, S.T. "Chemical Enhancement of Percutaneous Absorption in Relation to Stratum Corneum Structural Alterations"; J. Control Release, May 20, 1999; 59(2); 149-61.
Chikuno, T., "Plenty of launches at in Cosmetics 2003", COSSMA, Vo. 4, No. 3, pp. 30-32 (2003).
Michel, N., "The interest of amino acid biovector", In Cosmetics Exhibition & conference, Conference Proceedings, pp. 333-338 (Mar. 22-24, 1994).
Michel, N., "The interest of amino acid biovector", Agro Food Industry Hi Tech, vol. 5, No. 5, pp. 29-31 (Sep./Oct. 1994).
Michel, N., "The interest of amino acid biovector", Drug & Cosmetic Industry, vol. 159, No. 3, pp. 36-38, 40, 42, 104 (Sep. 1996).
Michel, N., "The interest of amino acid biovector", Active Ingredients Conference Proceedings, pp. 117-129 (Nov. 13-14, 1996).
Oikarinen, "The Aging of Skin: Chronoaging Versus Photoaging," Photodermatol. Photoimmunol. Photomed., vol. 7, pp. 3-4, (1990).

Mintel Database "Youth Body Cream", Guinot, Jun. 2010, 5 pages http://www.gnpd.com.
Mintel Database Jan. 2010 (Jan. 2010) "Neck and Decollete Care" 4 pages http://www.gnpd.com.
Mintel Database Jun. 2009 (Jun. 2009). "Moisturize Anti-Wrinkle Skin Firming Hydrator" April Rain Skin Science, 8 pages http://www.gnpd.com.
Mintel Database Apr. 2011 (Apr. 2011). "Enriched Body Care" Mary Cohr. 5 pages http://www.gnpd.com.
Mintel Database "High Performance Hair Growth Stimulating Conditioner", DS Laboratories Feb. 2011, 5 pages http://www.gnpd.com.
Matts, P. et al., "Spectrophotometric Intracutaneous Analysis (SIAscopy)", 3rd Edition Handbook of Cosmetic Science and Technology, Paye, M., Barel, A.N. and Maibach, H.I. (eds), Informa Healthcare USA, Inc., New York, 275-283, 2008.
Matts, P., New Insights Into Skin Appearance and Measurement, Journal of Investigative Dermatology Symposium Proceedings (2008), 13, 6-9.
Todd et al., "Volatile Silicone Fluids for Cosmetics", Cosmetics and Toiletries, 91:27-32 (1976).
Federal Register, vol. 43, No. 166, pp. 38206-38269, Aug. 25, 1978.
European Extended Search Report; App. No. 11 857 221.3; Jul. 17, 2014; 5 pages.
Katahira N et al "Enhancement of topical delivery of a lipophilic drug from charged multilamellar liposomes.", Journal of Drug Targeting 1999, vol. 6, No. 6, 1999, pp. 405-414.
Benson Heather A E: "Elastic Liposomes for Topical and Transdermal Drug Delivery", Current Drug Delivery, vol. 6, No. 3, Jul. 2009 (Jul. 2009), pp. 217-226.
Trotta M et al: "Elastic Liposomes for Skin Delivery of Dipotassium Glycyrrhizinate", International Journal of Pharmaceutics, Elsevier BV, NL, vol. 241, No. 2, Jul. 25, 2002 (Jul. 25, 2002), pp. 319-327.
Li S et al: "A novel transdermal fomulation of 18[betaj-glycyrrhetic acid with lysine for improving bioavailability and efficacy", Jan. 1, 2012, vol. 25, No. 5, Jan. 1, 2012 (Jan. 1, 2012), pp. 257-268.
Chen J et al: "Skin permeation behavior of elastic liposomes: Role of formulation ingredients", Expert Opinion on Drug Delivery 2013 Informa Healthcare GBR, vol. 10, No. 6, Jun. 2013 (Jun. 2013), pp. 845-856.
International Search Report PCT/US2014/023985 mailed Jul. 17, 2014 including the Written Opinion of the International Searching Authority, 12 pages.
Mary Cohr Nouvelle Jeunesse Serum, Mintel GNPD Record ID 1670831, published Nov. 2011, 5 pages.
Mary Cohr Enriched New Youth Body Care, Mintel GNPD Record ID 1874046, published Aug. 2012, 5 pages.
Shokubutsu Umareno Fruit Juice Treatment, Mintel GNPD Record ID 2040240, published Feb. 2013, 3 pages.
Enprani Premier Collagen Eye Cream, Mintel GNPD Record ID 1919273, published Nov. 2012, 3 pages.
Adrian C. Williams et al., Penetration Enhancers, Advanced Drug Delivery Reviews vol. 56 (2004), pp. 603-618.
Adrian C. Williams et al., Penetration Enhancers, Advanced Drug Delivery Reviews vol. 64 (2012), pp. 128-137.
Biana Godin et al., Transdermal skin delivery: Predictions for humans from in vivo, ex vivo and animal models, Advanced Drug Delivery Reviews 59 (2007), pp. 1152-1161.
Donald L. Bissett et al., Niacinamide: A B Vitamin that Improves Aging Facial Skin Appearance, Dermatol Surg vol. 31 (2005), pp. 860-865.
Z. Diana Draelos, Clinical Situations Conducive to Proactive Skin Health and Anti-Aging Improvement, Journal of Investigative Dermatology Symposium Proceedings (2008), vol. 13, pp. 25-27.
David W. Osborne et al., Skin Penetration Enhancers Cited in the Technical Literature, Pharmaceutical Technology (1997), pp. 58-66.
Inayat Bashir Pathan et al., Chemical Penetration Enhancers for Transdermal Drug Delivery Systems, Tropical Journal of Pharmaceutical Research vol. 8 (2) (2009), pp. 173-179.
T. Marjukka Suhonen et al., Chemical Enhancement of Percutaneous Absorption in Relation to Stratum Corneum Structural Alterations, Journal of Controlled Release 59 (1999), pp. 149-161.
All Office Actions, U.S. Appl. No. 13/300,035.

(56) References Cited

OTHER PUBLICATIONS

All Office Actions, U.S. Appl. No. 13/357,916.
All Office Actions, U.S. Appl. No. 13/886,436.
All Office Actions, U.S. Appl. No. 10/627,533.
All Office Actions, U.S. Appl. No. 13/298,985.
U.S. Appl. No. 14/518,365, filed Oct. 20, 2014, Tanaka.
U.S. Appl. No. 14/602,764, filed Jan. 22, 2015, Tanaka.

* cited by examiner

COSMETIC COMPOSITIONS AND METHODS PROVIDING ENHANCED PENETRATION OF SKIN CARE ACTIVES

TECHNICAL FIELD

Cosmetic compositions providing enhanced penetration of skin care actives are provided along with methods of use related thereto.

BACKGROUND

Vitamin B compounds, such as niacinamide, are well known cosmetic skin care agents that are believed to provide a variety of skin care benefits (see, e.g., Bissett et al. "Niacinamide: A B Vitamin that Improves Aging Facial Skin Appearance" and Draelos "Clinical Situations Conducive to Proactive Skin Health and Anti-Aging Improvement"). Some of the reported benefits include improvement in the appearance of facial skin texture, red blotchiness, hyperpigmentation, and the enhancement of skin barrier function. Given these benefits, there is a continuing desire to increase the amount of vitamin B compounds delivered into human skin from topically applied cosmetic compositions to further enhance the skin benefits provided by these compounds.

It is known that a rate limiting step in the percutaneous absorption of ingredients is their initial penetration into and across the stratum corneum, see, e.g., Suhonen et al., "Chemical Enhancement of Percutaneous Absorption In Relation To Stratum Corneum Structural Alterations", Suhonen et al., Journal of Controlled Release, 59 (1999), pgs 149-161. Suhohen et al. also observed that there are at least two potential pathways thru the stratum cornenum: 1) transcellular (i.e., across the corneocytes and the lipid matrix), and 2) intercellular (i.e., via the lipid domains between the corneocytes), with the intercellular route believed to be providing the principal route for the permeation of ingredients.

Skin penetration enhancers are well known. As far back as 1997, a literature review by Osborne et al. purported to find more than 275 chemical compounds cited as enhancing skin permeation (see, e.g., Osborne, David, "Skin Penetration Enhancers Cited in the Technical Literature, Pharmaceutical Technology", 1997, pp 58-66). Compounds identified by Osborne include various species of fatty alcohols, fatty acid esters, fatty acids, fatty alcohol ethers, enzymes, amines and amides, surfactants, n-methyl pyrrolidones, ionic compounds and various others. More recently, Williams et al. noted that "[n]umerous compounds have been evaluated for penetration enhancing activity, including sulphoxides (such as dimethylsulphoxide, DMSO), azones (e.g., laurocapram), pyrrolidones, (for example 2-pyrrolidone, 2P), alcohols and alkanols (ethanol, or decanol), glycols (for example propylene glycol, PG, a common excipient in topically applied dosage forms), surfactants (also common in dosage forms) and terpenes". Williams et al., "Penetration Enhancers", Advanced Drug Delivery Reviews 56, pgs 603-618 (2004), see also, Pathan et al., "Chemical Penetration Enhancers for Transdermal Drug Delivery Systems", Tropical Journal of Pharmaceutical Research, Vol. 8(2), pgs 173-179 (2009).

While various skin penetration enhancers are known, their mechanisms of action, particularly in the stratum corneum, are still being investigated. For example, Suhonen et al. postulated that "many penetration enhancers are capable of inserting between the hydrophobic tails of the bilayer, thus disturbing their packing, increasing their fluidity and, subsequently, leading to easier diffusion of lipid-like penetrants". Suhonen et al. also concluded however that "[a]lthough during the last 10 years an enormous amount of knowledge became available on the structure of the stratum corneum and the effect of solvent and penetration enhancers on this structure, still our knowledge on this tissue and its lipid organization is very limited". Similarly, Williams et al. noted in 2004 that the inclusion of penetration enhancers "into topical or transdermal formulations is limited since the underlying mechanisms of action of these agents are seldom clearly defined". Even more recently, Williams and Barry, "Penetration enhancers", Advanced Drug Delivery Reviews, Vol. 64, pgs 128-137 (2012), stated that "[i]t is difficult to select rationally a penetration enhancer for a given permeant." While the effects of certain individual ingredients on skin penetration has been studied to some degree, the role that combinations of ingredients might play in enhancing penetration of cosmetic agents into and thru the stratum corneum appears to be even less well studied, including how varying concentrations, ratios and/or combinations of ingredients might affect penetration of cosmetic skin ingredients.

SUMMARY

A cosmetic composition suitable for topical application is provided. In some embodiments, the cosmetic composition comprises glycerin, hexyldecanol, a vitamin B compound, and one or more materials selected from the group consisting of pentylene glycol, hexylene glycol, propylene glycol, triethylene glycol, butylene glycol, and hexanediol. In some embodiments, the ratio of the combination of glycerin, hexyldecanol, and one or more materials to the vitamin B compound is at least 2:1.

In some embodiments, the cosmetic composition comprises glycerin, hexyldecanol, and a vitamin B compound, wherein the concentration of hexyldecanol is greater than 3% by weight of cosmetic composition, and the concentration of the vitamin B compound is greater than 1% by weight of the cosmetic composition.

In some embodiments, the cosmetic composition comprises glycerin; a vitamin B compound; one or more materials selected from the group consisting of pentylene glycol, hexylene glycol, propylene glycol, triethylene glycol, butylene glycol, and hexanediol; and one or more penetration enhancers selected from the group consisting of hexyldecanol, butyldecanol, 4-methyl-5-decanol, 2-heptyldecanol, octyldecanol, decyltetradecanol, 2-butyl-1-octanol, 2-octyl-1-decanol, 2-dodecyl-1hexadecanol, and 2-tetradecylotadecanol. In some embodiments, the ratio of the combination of glycerin, hexyldecanol, and one or more materials to the vitamin B compound is at least 2:1.

A method of using a cosmetic composition of using the composition is also provided. At least one method may comprise applying a cosmetic composition to a facial skin surface in need of treatment, wherein the cosmetic composition comprises: glycerin; one or more materials selected from the group consisting of 1,2-pentanediol, 1,4-pentanediol, 2,4-pentanediol, 1,5-pentanediol, 1,2-butanediol, 1,3-butanediol, 1,4-butanediol, 2,3-butanediol, 1,2-hexanediol, 1,5-hexanediol, 1,6-hexanediol, 2,5-hexanediol, hexylene glycol, and combinations thereof; hexyldecanol; a vitamin B compound; and wherein the ratio of the combination of i) and ii) and iii) to iv) in the skin care composition is at least 2:1.

BRIEF DESCRIPTION OF THE DRAWINGS

While the specification concludes with claims, it is believed that the same will be better understood from the following description taken in conjunction with the accompanying drawings in which:

DETAILED DESCRIPTION

Figure 1:
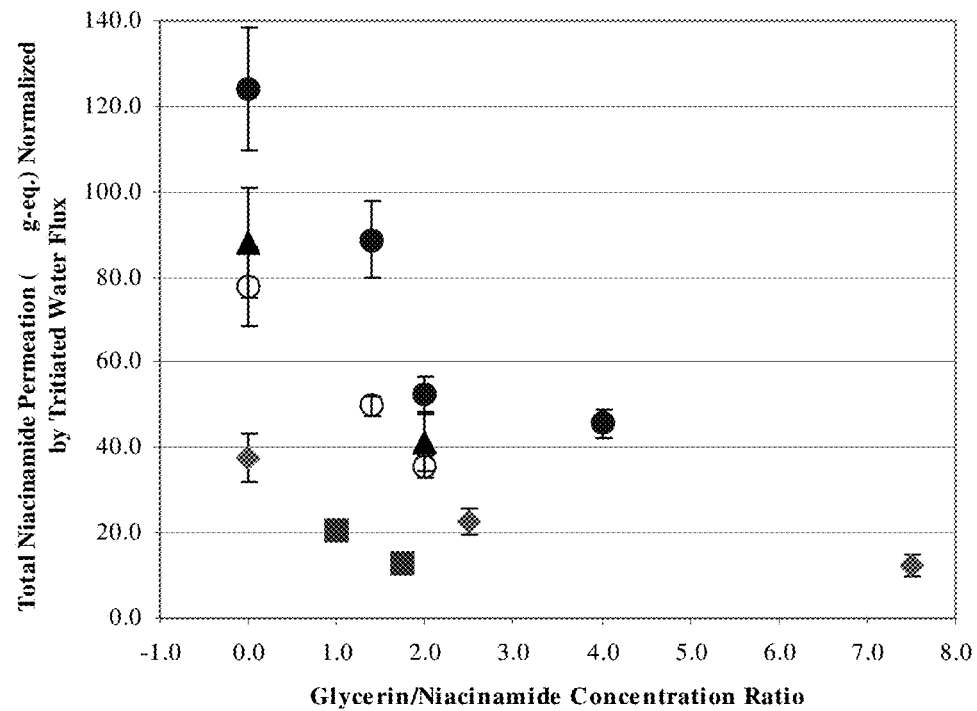
FIG. 1 is a graph of total niacinamide penetration versus glycerin/niacinamide concentration ratio for four cosmetic compositions.

Described hereafter are various embodiments of cosmetic compositions providing enhanced penetration of vitamin B compounds into the stratum corneum. It has been surprisingly discovered that it is possible to enhance penetration by combining certain ingredients and/or ratios/concentrations of ingredients in a skin care composition.

As used herein, vitamin B compounds include B1 compounds, B2 compounds, B3 compound, B5 compounds, such as panthenol or "pro-B5", pantothenic acid, pantothenyl; B6 compounds, such as pyroxidine, pyridoxal, pyridoxamine, carnitine, thiamine, and riboflavin. In some embodiments, the vitamin B compound is a B3 compound having the formula:

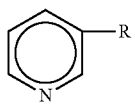

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

As used herein, the term diol refers to a compound comprising two hydroxyl groups bonded to different carbon atoms and having the general formula R—OH. A diol may be linear or branched, the hydroxyl groups may be on adjacent or non-adjacent carbon atoms, and the carbon bonds may include single and/or double bonds. In some embodiments, the diol may be linear and has a carbon chain length from between 4 and 6 atoms (C4 to C6), optionally with one or more branched methyl groups ($CH_3$).

I. IN VITRO OBSERVATIONS RELATING TO A VITAMIN B COMPOUND AND GLYCERIN

Topical application of niacinamide, which is soluble in both water and glycerin, can be associated with a variety of cosmetic skin care benefits. These may include: i) normalization of age associated depletions of nicotinamide coenzymes in skin, ii) up-regulation of epidermal ceramide synthesis with concurrent epidermal barrier benefits, iii) protection against damage produced by UV irradiation, iv) inhibition of the transfer of melanosomes from melanocytes to keratinocytes (thereby providing a potential skin tone benefit), and reduction in sebaceous lipogenesis. These activities may improve the appearance of aging/photo-damaged skin.

Glycerin is a small, polar molecule that is liquid at room temperature and miscible with water. Endogenous glycerin is believed to be an important component of skin hydration and topical application of cosmetic products containing glycerin can be associated with improvements in barrier function, induction of biomarkers associated with keratinocyte proliferation and wound healing, reduction in melanin intensity, increases in epidermal thickness, and improvements in general skin appearance.

Given the cosmetic benefits likely provided by glycerin and vitamin B compounds, it is often desirable to combine both in cosmetic compositions. However, it is has been observed that the presence of glycerin in such a cosmetic composition can retard the penetration of niacinamide into the skin. Referring to Example 1, it has been observed that increasing glycerin concentrations can decrease niacinamide skin penetration from a variety of cosmetic compositions. In Example 1, a series of in vitro skin penetration studies were conducted over a 6 hr time period to assess the impact of glycerin upon the penetration of radiolabeled niacinamide from several cosmetic compositions, including an oil-water emulsion, a water-in-silicone emulsion, and a water gel. The cosmetic compositions were topically applied to split-thickness human cadaver skin. A Franz diffusion cell system was used to measure the amount of penetration of the radiolabeled niacinamide thru the cadaver skin. The kinetics of in vitro radiolabeled niacinamide skin penetration were observed at fixed glycerin concentrations, and the impact of glycerin and niacinamide concentrations upon the penetration of radiolabeled niacinamide and glycerin over 6 hours were measured. In addition, niacinamide penetration was measured as a function of glycerin concentration.

Referring to FIG. 1, total niacinamide penetration as a function of the glycerin/niacinamide ratio for the four cosmetic compositions tested in Example 1 are plotted. The data suggests that the addition of glycerin decreases niacinamide penetration from a variety of cosmetic compositions. Further, the data suggests that increasing glycerin concentration incrementally decreases niacinamide skin penetration from a variety of cosmetic compositions.

II. IN SILICO OBSERVATIONS RELATING TO A VITAMIN B COMPOUND AND GLYCERIN

Figure 2:
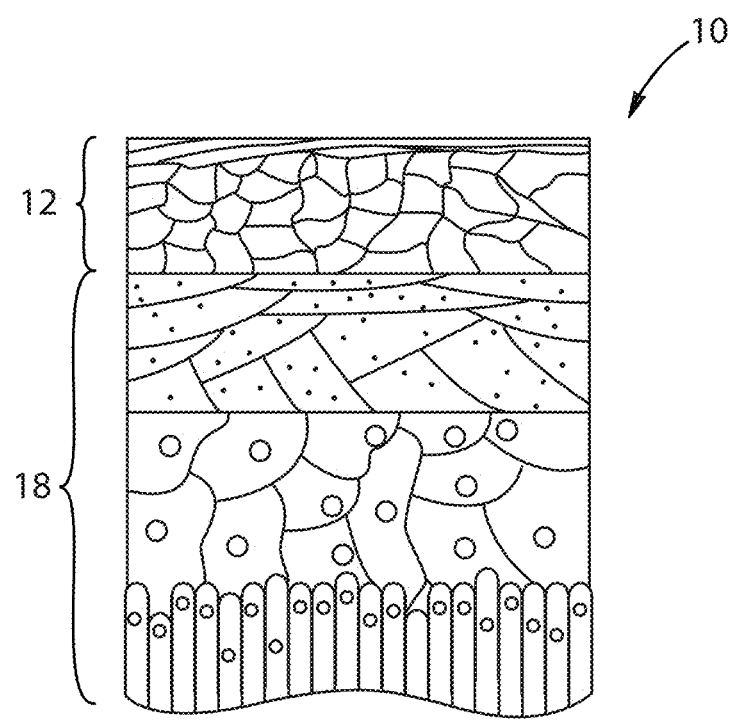
FIG. 2 is a schematic representation of the epidermal and dermal layers of human skin.
Figure 3:
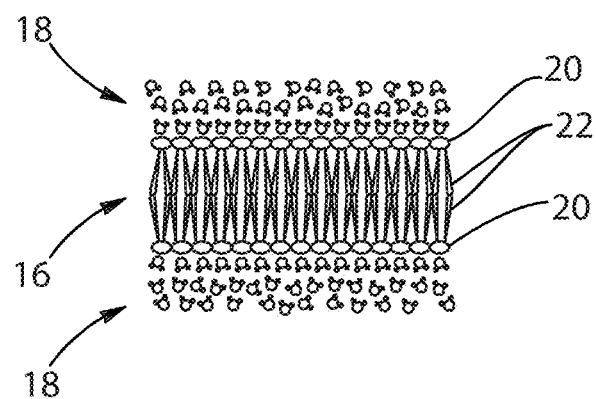
FIG. 3 is a schematic representation of lipid bilayers and water channels of the stratum corneum.

Referring to FIG. 2, a schematic representation of the epidermal and dermal skin layers is shown. The outer most layer of the epidermis 10 is the stratum corneum 12. Below the stratum corneum lies the stratum lucidum, the stratum granulosum, the stratum spinosum, and the stratum basale layers (collectively, reference numeral 18). Referring to FIG. 3, the stratum corneum comprises lipid bilayers 16 and water channels 18. The lipid bilayers 16 predominantly comprise ceramides, cholesterol, and free fatty acid (FFA) mixtures arranged in a highly matrixed head/tail configuration, represented by the head groups 20 and tail groups 22, shown schematically in FIG. 3.

Figure 4:
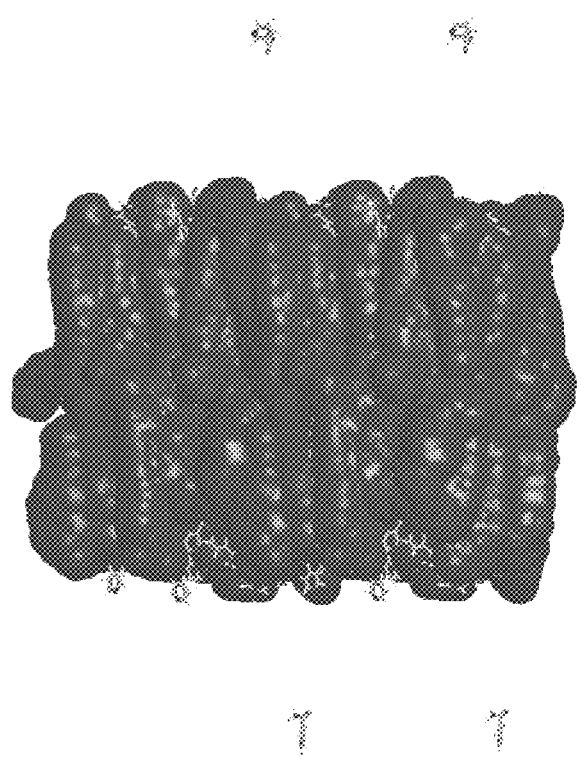
FIG. 4 is a graphic depiction from an in silico model of a lipid bilayer and water channels of the stratum corneum, wherein molecules of niacinamide are shown.
Figure 5:
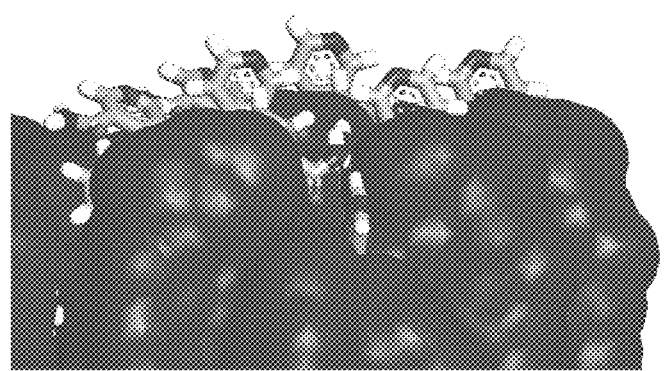
FIG. 5 is an enlargement of a portion of the lipid bilayer shown in FIG. 5, wherein niacinamide molecules are shown embedded in the head groups of the lipid bilayer.
Figure 6:
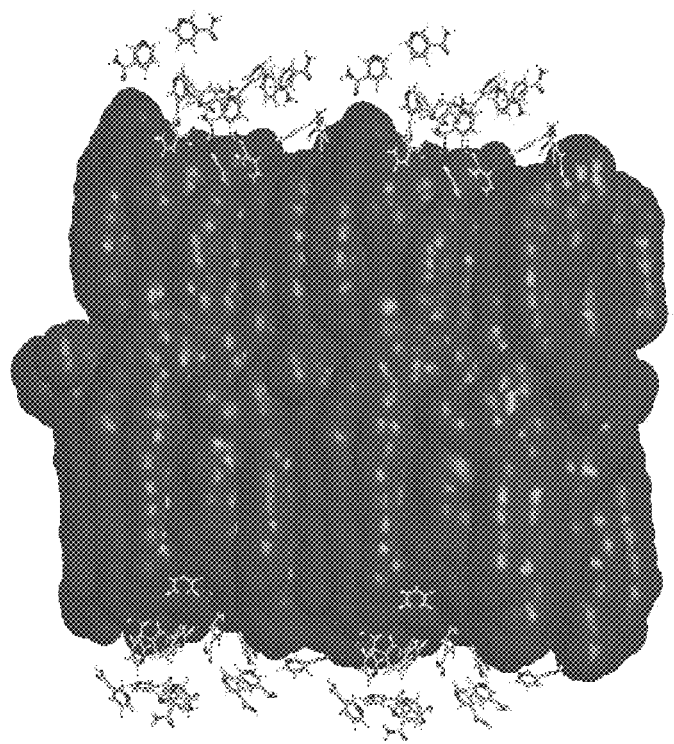
FIG. 6 graphic depiction from an in silico model of a lipid bilayer and water channels of the stratum corneum, wherein molecules of niacinamide are shown within the water channels following introduction of glycerin into the water channels.
Figure 7:
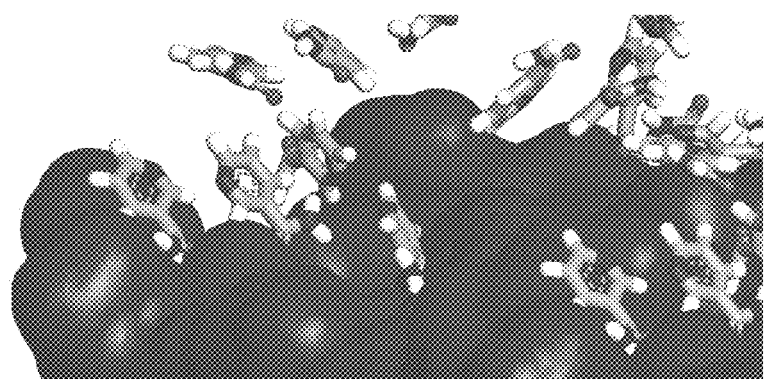
FIG. 7 is an enlargement of a portion of the lipid bilayer shown in FIG. 7.

Referring to FIGS. 4 and 5, atomistic, in-silico modeling of a lipid bilayer region suggests a possible explanation for the in vitro glycerin effect previously discussed, namely the effect of decreasing niacinamide penetration into the skin when glycerin is present in a cosmetic composition. FIGS. 4 and 5 illustrate an in silico model of the lipid bilayer region of the stratum corneum, where heads groups and tails groups of the lipids are shown in a packed arrangement. In between the opposing head groups are the water channels. The in silico model suggests that niacinamide molecules, when only interacting with water molecules of the water channels, will distribute themselves between sitting on the head group surface of the lipid bilayer and dissolving in the water of the water channels. In comparison, FIGS. 6 and 7 illustrate the effect of glycerin on niacinamide in the water channels. It appears that glycerin favorably binds to the hydrophilic head groups of the lipid bilayers and to itself via effective H-bonding and networking, thereby essentially "gelling" the water channel and entrapping the niacinamide molecules within the water channels to retard penetration of niacinamide through the water channels.

While it is has been observed, both in vitro and in silico, that glycerin may sometimes be an impediment to the penetration of niacinamide thru the skin, it has been surprisingly discovered that certain ingredient(s), such as hexyldecanol (e.g. 2-hexyl-1-decanol) and/or certain diols, may counteract this effect and in fact may, in some instances, enable glycerin to synergistically enhance rather than retard penetration of niacinamide into and thru the stratum corneum. Still further, empirical evidence suggests that particular ratios/concentrations of ingredients may be more effective at enhancing the penetration of vitamin B compounds into and thru the stratum corneum.

III. VITAMIN B COMPOUNDS, GLYCERIN, AND HEXYLDECANOL

It has been surprisingly observed in vitro that the addition of glycerin to a cosmetic composition comprising hexyldecanol can increase, rather than decrease, the penetration of radiolabeled niacinamide thru split thickness human cadaver skin. Tables 1-7 below summarize the total percentage dose of niacinamide recovered from the combination of the epidermis, dermis, and the Franz Cell Receptor (which represents total niacinamide penetration thru the skin during the test period) after application of the cosmetic compositions set forth in Tables 9-11.

Referring to Example 2, penetration of radiolabeled niacinamide into cadaver skin was assessed over a 24 hour time period using a Franz diffusion cell system, which is a well known device in the art for measuring penetration of compounds into skin samples. Table 1 below summarizes the total percentage dose of niacinamide recovered from the combination of the epidermis, dermis, and the Franz Cell Receptor (which represents total niacinamide penetration thru the skin during the test period) after application of the cosmetic compositions set forth in Examples 2A, 2B, 2C, and 2D. Six replicates were tested for each cosmetic composition. In addition, Table 1 sets forth the ratio of the concentrations of glycerin/hexyldecanol to niacinamide and total concentration of glycerin/hexyldecanol in the cosmetic composition. The cosmetic composition of Example 2A included 5% niacinamide. The cosmetic composition of Example 2B included 5% niacinamide (shown in Table as "N") and 7% glycerin (shown in Table as "G"). The cosmetic composition of Example 2C included 5% niacinamide and 5% hexyldecanol (shown in Table as "HD"), and the cosmetic composition of Example 2D included 5% niacinamide, 7% glycerin, and 5% hexyldecanol.

TABLE 1

|  | Example 2A 5% N | Example 2B 5% N/7% G | Example 2C 5% N/5% HD | Example 2D 5% N/7% G/ 5% HD |
|---|---|---|---|---|
| Ratio | NA | 1.4 | 1 | 2.4 |
| Total Concentration | NA | 7% | 5% | 12% |
| Sample #1 | 15.94 | 32.43 | 64.16 | 64.29 |
| Sample #2 | 22.01 | 38.04 | 53.58 | 91.75 |
| Sample #3 | 36.81 | 20.91 | 74.96 | 72.08 |
| Sample #4 | 29.61 | 29.43 | 64.39 | 93.78 |
| Sample #5 | 44.98 | 32.60 | 50.40 | 68.24 |
| Sample #6 | 52.56 | 30.64 | 30.85 | 46.33 |
| Avg | 33.65 | 30.68 | 56.39 | 72.74 |
| Stdv | 13.87 | 5.62 | 15.27 | 17.85 |
| P value |  | 0.64 | 0.02 | 0.002 |

Comparing Examples 2A and 2B, it appears that the addition of 7% glycerin resulted in no increase to a slight decrease in average niacinamide penetration, consistent with the observations previously discussed for Example 1 over a shorter 6 hour time period. While the p-value and standard deviation values are somewhat high, it is believed this data still tends to support the general directionality of the observation. Comparing Examples 2A and 2C, the addition of 5% hexyldecanol resulted in an increase in average niacinamide penetration from 33.65% to 56.39%. However, comparing Examples 2A and 2D, the addition of both 7% glycerin and 5% hexyldecanol resulted in an increase in average niacinamide penetration to 72.74%. Surprisingly, it appears that the negative effect that glycerin can have on niacinamide penetration can be reduced or mitigated by adding hexyldecanol to a cosmetic composition. Further, it appears that, in at least some instances, glycerin in the presence of hexyldecanol can increase rather than decrease average niacinamide penetration. Further, to achieve at least a doubling of average niacinamide penetration, it appears that a ratio of around 2:1 (or greater) of the concentrations of glycerin/hexyldecanol to niacinamide may be beneficial.

Referring to Table 2 below, the effect of increasing hexyldecanol concentration on niacinamide penetration, in the absence of glycerin, on human cadaver skin is illustrated. Example 2E included 5% niacinamide and 10% hexyldecanol, while Example 2F included 5% niacinamide and 15% hexyldecanol.

TABLE 2

| Sample | Example 2A 5% N | Example 2C 5% N/5% HD | Example 2E 5% N/10% HD | Example 2F 5% N/15% HD |
|---|---|---|---|---|
| #1 | 15.94 | 64.16 | 55.21 | 87.11 |
| #2 | 22.01 | 53.58 | 42.04 | 85.95 |
| #3 | 36.81 | 74.96 | 61.74 | 60.81 |
| #4 | 29.61 | 64.39 | 87 | 93.17 |
| #5 | 44.98 | 50.40 | 88.22 | 70.59 |
| #6 | 52.56 | 30.85 | 88.32 | 80.12 |
| Avg | 33.65 | 56.39 | 70.42 | 79.63 |
| Stdv | 13.87 | 15.27 | 20.12 | 11.96 |
| P value |  | 0.02 | 0.004 | 0.0001 |

Comparing Examples 2A and 2C, the addition of 5% hexyldecanol increased average niacinamide penetration from 33.65% to 56.39%. Comparing Examples 2A and 2E, the addition of 10% hexyldecanol increased average niacinamide penetration to 70.42% from 33.65%. Finally, comparing Examples 2A and 2F, the addition of 15% hexyldecanol increased average niacinamide penetration from 33.65% to 79.63%. This data appears to suggest a slowing of the rate of increase of the niacinamide penetration benefit from increasing hexyldecanol concentration.

Referring to Table 3 below, the effect of increasing hexyldecanol concentration on niacinamide penetration, in the presence of glycerin, on human cadaver skin is illustrated. Table 4 summarizes the total percentage dose of niacinamide recovered from the combination of the epidermis, dermis, and the Franz Cell Receptor after application of the cosmetic compositions set forth in Examples 2B, 2D, 2G, and 2H. The cosmetic composition of Example 2G included 5% niacinamide, 7% glycerin, and 10% hexyldecanol; and the cosmetic composition of Example 2H included 5% niacinamide, 7% glycerin, and 15% hexyldecanol.

TABLE 3

| Sample | Example 2B 5% N/7% G | Example 2D 5% N/7% G/ 5% HD | Example 2G 5% N/7% G/ 10% HD | Example 2H 5% N/7% G/ 15% HD |
| --- | --- | --- | --- | --- |
| #1 | 32.43 | 64.29 | 70.67 | 83.86 |
| #2 | 38.04 | 91.75 | 80.15 | 83.77 |
| #3 | 20.91 | 72.08 | 68.88 | 77.68 |
| #4 | 29.43 | 93.78 | 75.56 | 68.58 |
| #5 | 32.60 | 68.24 | 80.65 | 74.74 |
| #6 | 30.64 | 46.33 | 83.31 | 88.03 |
| Avg | 30.68 | 72.74 | 76.54 | 79.44 |
| Stdv | 5.62 | 17.85 | 5.83 | 7.14 |
| P value | 0.64 | 0.002 | <0.0001 | <0.0001 |

Comparing Examples 2B and 2D, the addition of 5% hexyldecanol increased average niacinamide penetration from 30.68% to 72.74%. Comparing Examples 2B and 2G, the addition of 10% hexyldecanol increased average niacinamide penetration from 30.68% to 76.54%. Comparing Examples 2B and 2H, the addition of 15% hexyldecanol increased average niacinamide penetration to 79.44%, which appears to suggest (although less strongly than shown by the data in Table 2) a slowing of the rate of increase of the penetration benefit from increasing hexyldecanol concentration in the presence of glycerin. It also appears that as hexydecanol concentration increases (for fixed glycerin concentrations), the positive effect on niacinamide penetration by glycerin decreases. For example, comparing again Examples 2C and 2D, niacinamide penetration increased from 56.39% to 72.74% with the addition of 7% glycerin in the presence of 5% hexyldecanol. Comparing Examples 2E (Table 3) and 2G (Table 4), the addition of 7% glycerin in the presence of 10% hexydecanol resulted in a modest average increase in niacinamide penetration from 70.42% to 76.54%. Comparing Examples 2F (Table 3) and 2H (Table 4), the addition of 7% glycerin in the presence of 15% hexyldecanol resulted in no appreciable average increase in niacinamide penetration (79.63% v. 79.44%).

This data appears to support the proposition previously discussed that the negative impact that glycerin can have on niacinamide penetration can be reduced or mitigated by the addition of hexyldecanol. Further, this data would appear to suggest that the increase in niacinamide penetration observed when comparing Examples 2C and 2D appears to erode as the concentration of hexyldecanol increases at a fixed glycerin concentration. Without intending to be bound by any theory, it appears that relatively higher concentrations of hexyldecanol (and/or ratios of hexyldecanol to glycerin) may provide a diminishing incremental improvement in niacinamide penetration in the presence of glycerin. It also seems possible that relatively lower concentrations of hexyldecanol may not overcome the observed effect of glycerin retarding niacinamide penetration if the concentration of glycerin is too great.

Thus, in some embodiments, the cosmetic compositions described herein may have a concentration of hexyldecanol greater than 0.5%, 1%, 2%, 3%, 4%, 5%, 6%, 8%, 10% or 12% and/or less than 20%, 18%, 16%, 15% or 14% by weight of the cosmetic composition. In some embodiments, the cosmetic compositions described herein may have a concentration of hexyldecanol greater than about 0.5%, 1%, 2%, 3%, 4%, 5%, 6%, 8%, 10% or 12% and/or less than about 20%, 18%, 16%, 15% or 14% by weight of the cosmetic composition. Further, in some embodiments, the cosmetic compositions have a ratio of hexyldecanol to glycerin of greater than 0.75:1; 1:1; or 1.25:1 and/or less than 2.5:1, 2:1, 1.75:1: or 1.5:1. Further, in some embodiments, the cosmetic compositions have a ratio of hexyldecanol to glycerin of greater than about 0.75:1, 1:1, or 1.25:1 and/or less than about 2.5:1, 2:1, 1.75:1, or 1.5:1. Still further, in some embodiments, the cosmetic compositions can have a concentration of glycerin, by weight of the cosmetic composition, of greater than 4%, 5%, 6%, 7%, 8%, 10%, 12%, 15%, 20% and/or less than 30%, 25%, or 20% in combination with hexyldecanol. Still further, the cosmetic compositions can also have a concentration of glycerin, by weight of the cosmetic composition, of greater than about 4%, 5%, 6%, 7%, 8%, 10%, 12%, 15%, 20% and/or less than about 30%, 25%, or 20% in combination with hexyldecanol. In some embodiments, the cosmetic compositions have a concentration of a vitamin B compound, by weight of the cosmetic composition, of greater than 1%, 2%, 3%, 4%, or 5% and/or less than 10%, 8%, or 6%. In some embodiments, the cosmetic compositions have a concentration of a vitamin B compound, by weight of the cosmetic composition, of greater than about 1%, 2%, 3%, 4%, or 5% and/or less than about 10%, 8%, or 6%. It is believed that higher, rather than lower, concentrations of the vitamin B compound are preferred in order to improve the likelihood of a detectable in vivo skin benefit from the niacinamide. In some embodiments, the cosmetic composition has an average vitamin B total recovery, as a percentage of total dose using a Franz cell test method, greater than 50%, 60%, or 70% and/or less than 85%, 80% or 70%.

Alternatively, hexyldecanol may be replaced or combined with butyldecanol. For example, the butyldecanol may have the following formula:

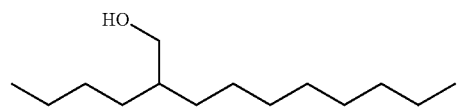

Alternatively, hexyldecanol may be replaced or combined with 4-methyl-5-decanol. For example, 4-methyl-5-decanol may have the following formula:

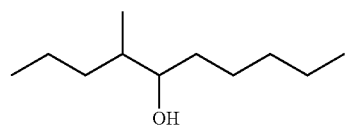

Alternatively, hexyldecanol may be replaced or combined with 2-heptyldecanol. For example, 2-heptyldecanol may have the following formula:

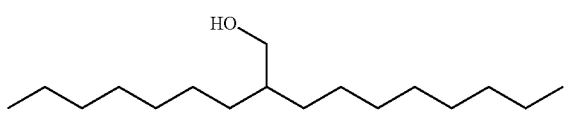 [SMILES: CCCCCCCCC(CO)CCCCCCC]

Alternatively, hexyldecanol may be replaced or combined with octyldecanol. For example, octyldecanol may have the following formula:

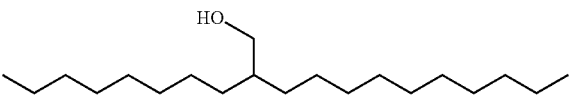 [SMILES: CCCCCCCCCCC(CO)CCCCCCCC]

Alternatively, hexyldecanol may be replaced or combined with decyltetradecanol. For example, decyltetradecanol may have the following formula:

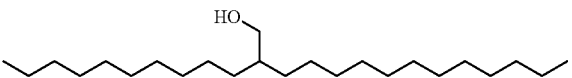 [SMILES: CCCCCCCCCCCCC(CO)CCCCCCCCCC]

Alternatively, hexyldecanol may be replaced or combined with 2-butyl-1-octanol. For example, 2-butyl-1-octanol may have the following formula:

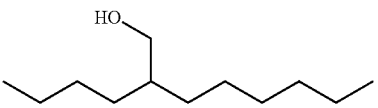

Alternatively, hexyldecanol may be replaced or combined with 2-octyl-1-decanol. For example, 2-octyl-1-decanol may have the following formula:

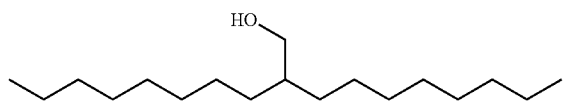 [SMILES: CCCCCCCCC(CO)CCCCCCCC]

Alternatively, hexyldecanol may be replaced or combined with 2-dodecyl-1-hexadecanol. For example, 2-dodecyl-1-hexadecanol may have the following formula:

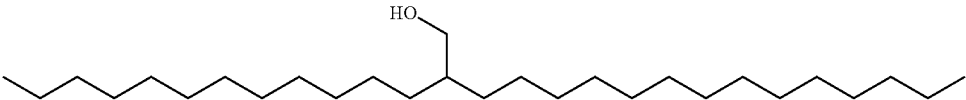 [SMILES: CCCCCCCCCCCCCCC(CO)CCCCCCCCCCCC]

Alternatively, hexyldecanol may be replaced or combined with 2-tetradecyloctadecanol. For example, the 2-tetradecyloctadecanol may have the following formula:

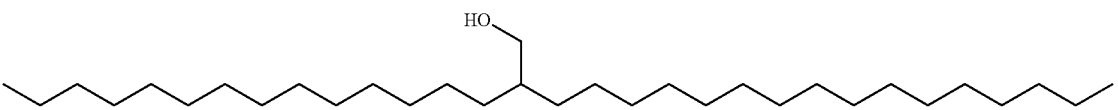 [SMILES: CCCCCCCCCCCCCCCCC(CO)CCCCCCCCCCCCCC]

Alternatively, hexyldecanol may be replaced or combined with a mixture including two or more of butyldecanol, 4-methyl-5-decanol, 2-heptyldecanol, octyldecanol, decyltetradecanol, 2-butyl-1-octanol, 2-octyl-1-decanol, 2-dodecyl-1-hexadecanol, and 2-tetradecyloctadecanol.

IV. VITAMIN B COMPOUNDS, HEXYLDECANOL, GLYCERIN AND VARIOUS DIOLS

It has also been discovered that some liquid diols can further increase niacinamide penetration when combined with hexyldecanol and glycerin and that, in some embodiments, certain ratios and concentrations of ingredients may be desirable. These discoveries can allow a cosmetic composition formulator to customize a cosmetic composition to achieve varying degrees of penetration of a vitamin B compound in the presence of glycerin while providing significant formulation flexibility. For example, by combining certain ingredients, it may be possible to achieve superior penetration of a vitamin B compound while lowering the individual (and total combined) concentrations of the operative ingredients, thereby allowing "more space" in the formulation for the inclusion of other materials. Alternatively, by including certain ingredients versus others, a formulator may be able to better tailor the formulation to achieve desired aesthetics. Some of the diols include, but are not limited to, various forms of pentylene glycol, butylene glycol, hexylene glycol, hexanediol, propylene glycol, triethylene glycol, and combinations thereof. In some embodiments, the diols may include 1,2-pentanediol; 1,4-pentanediol; 2,4-pentanediol; 1,5-pentanediol; 1,2-butanediol; 1,3-butanediol; 1,4-butanediol; 2,3-butanediol; 1,2-hexanediol; 1,5-hexanediol; 1,6-hexanediol; 2,5-hexanediol; hexylene glycol; and combinations thereof. Diols that are liquid at room temperature are believed to be better at solubilizing the vitamin B compound and enhancing the transport of the niacinamide and/or hexyldecanol from the cosmetic composition and into the stratum corneum.

Referring to Example 3, penetration of radiolabeled niacinamide into cadaver skin was assessed using the same Franz Diffusion Cell system as previously discussed for Example 2. Table 4 below summarizes the total percentage dose of niacinamide recovered from the combination of the epidermis, dermis, and the Franz Cell Receptor after application of the cosmetic compositions set forth in Examples 2H, 3A, 3B, 3C, and 3D. In addition, Table 4 sets forth the ratio of the concentrations of diols/glycerin/hexyldecanol to niacinamide, and total concentration of diols/glycerin/hexyldecanol in the cosmetic composition. The cosmetic composition of Example 3A included 5% niacinamide, 7% glycerin, 6% pentylene glycol and 5% hexyldecanol. The cosmetic composition of Example 3B included 5% niacinamide, 7% glycerin, 1% hexanediol, and 5% hexyldecanol. The cosmetic composition of Example 3C included 5% niacinamide, 7% glycerin, 6% pentylene glycol, 1% hexanediol, and 5% hexyldecanol.

TABLE 4

| Sample | Example 2H 5% N/7% G/ 15% HD | Example 3A 5% N/7% G/6% PG/ 5% HD | Example 3B 5% N/7% G/1% H/ 5% HD | Example 3C 5% N/7% G/6% PG/ 1% H/5% HD |
|---|---|---|---|---|
| Ratio | 4.4 | 3.6 | 2.6 | 3.8 |
| Total Concentration | 22% | 18% | 13% | 19% |
| #1 | 83.86 | 75.06 | 78.52 | 94.66 |
| #2 | 83.77 | 74.95 | 80.29 | 91.39 |
| #3 | 77.68 | 85.94 | 69.25 | 85.5 |
| #4 | 68.58 | 88.89 | 79.63 | 84.54 |
| #5 | 74.74 | 85.21 | 89.70 | 96.23 |
| #6 | 88.03 | 84.21 | 95.63 | 89.84 |
| Avg | 79.44 | 82.38 | 82.17 | 90.36 |
| Stdv | 7.14 | 5.92 | 9.25 | 4.73 |
| P value | <0.0001 | <0.0001 | <0.0001 | <0.0001 |

Comparing Examples 3A and 2H, the cosmetic composition of Example 3A provided similar (or slightly superior) average niacinamide penetration results with 5% hexyldecanol and 18% total concentration of diols/glycerin/hexyldecanol as Example 2H, which included 15% hexyldecanol and 22% total concentration of diols/glycerin/hexyldecanol. Example 3B provided similar average niacinamide penetration results to Examples 3A and 2H, with the lowest total concentration of diols/glycerin/hexyldecanol (13% v. 18% and 22%). Example 3C provided superior average niacinamide penetration results to Example 2H with a lower total concentration of diols/glycerin/hexyldecanol (19% v. 22%). Surprisingly, this data suggests that it is possible to achieve superior (and/or more efficient) niacinamide penetration in the presence of glycerin by combining hexyldecanol with diols such as pentylene glycol and/or hexanediol versus merely increasing the concentration of hexyldecanol to achieve a penetration increase.

Table 5 below summarizes the total percentage dose of niacinamide recovered from the combination of the epidermis, dermis, and the Franz Cell Receptor after application of the cosmetic compositions set forth in Examples 2A, 2B, 2D, 3D, and 3E. The cosmetic composition of Example 3D included 5% niacinamide, 7% glycerin, and 6% pentylene glycol, and the cosmetic composition of Example 3E included 5% niacinamide and 6% pentylene glycol.

TABLE 5

| Sample | Example 2A 5% N | Example 2B 5% N/ 7% G | Example 2D 5% N/7% G/ 5% HD | Example 3D 5% N/7% G/ 6% PG | Example 3E % N/ 56% PG |
|---|---|---|---|---|---|
| #1 | 15.94 | 32.43 | 64.29 | 19.94 | 38.46 |
| #2 | 22.01 | 38.04 | 91.75 | 49.83 | 72.31 |
| #3 | 36.81 | 20.91 | 72.08 | 34.60 | 32.52 |
| #4 | 29.61 | 29.43 | 93.78 | 22.50 | 70.60 |
| #5 | 44.98 | 32.60 | 68.24 | 40.59 | 33.74 |
| #6 | 52.56 | 30.64 | 46.33 | 49.06 | 84.43 |
| Avg | 33.65 | 30.68 | 72.74 | 36.09 | 55.34 |
| Stdv | 13.87 | 5.62 | 17.85 | 12.85 | 22.97 |
| P value | — | 0.64 | 0.002 | 0.76 | 0.08 |

Comparing Examples 2B and 3D, the addition of pentylene glycol resulted in an increase in the average niacinamide penetration (36.09% v. 30.68%) in the presence of glycerin. However, comparing Examples 3E and 2A, this increase was not nearly as great as provided by the addition of pentylene glycol in the absence of glycerin. This data would tend to support the prior observation that the presence of glycerin in a cosmetic composition can retard penetration of niacinamide thru the skin. This data would also suggest that adding pentylene glycol to a cosmetic composition containing glycerin can result in a modest increase in average niacinamide penetration but not nearly as significant as observed by the addition of a similar concentration of hexyldecanol. For example, comparing Examples 2D and 3D, the addition of hexyldecanol provided a superior average niacinamide penetration result compared to that achieved by the addition of pentylene glycol (72.74% v. 36.09%), despite the fact that the added concentration of hexyldecanol was slightly lower than the pentylene glycol concentration (5% v. 6%).

Table 6 below summarizes the total percentage dose of niacinamide recovered from the combination of the epidermis, dermis, and the Franz Cell Receptor after application of the cosmetic compositions set forth in Examples 2A, 3E, 3F, and 3G. The cosmetic composition of Example 3F included 5% niacinamide and 1% hexanediol. The cosmetic composition of Example 3G included 5% niacinamide and 3% hexylene glycol.

TABLE 6

| Sample | Example 2A 5% N | Example 3E 5% N/6% PG | Example 3F 5% N/ 1% Hexanediol | Example 3G 5% N/3% Hexylene Glycol |
|---|---|---|---|---|
| #1 | 15.94 | 38.46 | 33.94 | 46.94 |
| #2 | 22.01 | 72.31 | 34.95 | 43.44 |
| #3 | 36.81 | 32.52 | 52.73 | 50.21 |
| #4 | 29.61 | 70.6 | 31.77 | 38.96 |
| #5 | 44.98 | 33.74 | 80.83 | 39.77 |
| #6 | 52.56 | 84.43 | 80.56 | 38.1 |
| Avg | 33.65 | 55.34 | 52.46 | 42.9 |
| Stdv | 13.87 | 22.97 | 23.12 | 4.87 |
| P value | | 0.08 | 0.12 | 0.15 |

Notably, the average penetration of niacinamide increased in all the Examples compared to Example 2A. Thus, it seems possible that these materials could at least marginally improve the penetration of niacinamide in the presence of glycerin and hexyldecanol. Comparing Examples 3E and 3F, hexanediol appears to be much more efficient than pentylene glycol at increasing the average penetration of niacinamide at a given concentration, as hexanediol achieved a penetration result close to that of pentylene glycol with only a 1% concentration versus a 6% concentration of pentylene glycol. Comparing Examples 3E and 2C (Table 2), while both hexyldecanol and pentylene glycol increased average niacinamide penetration similarly in the absence of glycerin, the combination of hexydecanol and glycerin (Example 2D, Table 3) provided a superior penetration benefit to the combination of pentylene glycol and glycerin (Example 3D, Table 5) at similar concentrations. Comparing Examples 3E and 3D (Table 5), the addition of 7% glycerin in Example 3D resulted in a decrease in average niacinamide penetration from 55.32% to 36.09%, which tends to support the previously discussed observations of a niacinamide penetration decrease from resulting from the addition of glycerin.

Table 7 below summarizes the total percentage dose of niacinamide recovered from the combination of the epidermis, dermis, and the Franz Cell Receptor after application of the cosmetic compositions set forth in Examples 4A-4G. The cosmetic composition of Example 4A included 5% niacinamide, 2% butylene glycol, and 3% pentylene glycol. The cosmetic composition of Example 4B included 5% niacinamide, 7% glycerin, 5% hexyldecanol, 3% butylene glycol, 6% pentylene glycol, 3% hexylene glycol, and 1% hexanediol (shown as "XD" in Table 7). The cosmetic composition of Example 4C included 5% niacinamide, 7% glycerin, 5% hexyldecanol, 3% propylene glycol, and 1.5% hexylene glycol. The cosmetic composition of Example 4D included 5% niacinamide, 7% glycerin, 5% hexyldecanol, 3% pentylene glycol, and 1.5% hexylene glycol. The cosmetic composition of Example 4E included 5% niacinamide, 7% glycerin, 5% hexyldecanol, 3% triethylene glycol (shown as "TG" in Table 7), and 1.5% hexylene glycol.

TABLE 7

| Sample | 4A 5% N/ 2% BG/ 3% PG | 4B 5% N/ 7% G/ 5% HD/ 3% BG/ 6% PG/ 3% HG/ 1% XD | 4C 5% N/ 7% G/ 5% HD/ 3% PrG/ 1.5% HG | 4D 5% N/ 7% G/ 5% HD/ 3% PG/ 1.5% HG | 4E 5% N/ 7% G/ 5% HD/ 3% TG/ 1.5% HG |
| --- | --- | --- | --- | --- | --- |
| #1 | 40.99 | 91.05 | 81.68 | 59.00 | 71.19 |
| #2 | 60.84 | 92.30 | 60.99 | 74.91 | 78.19 |
| #3 | 31.32 | 81.66 | 85.69 | 72.21 | 63.80 |
| #4 | 39.35 | 91.61 | 64.03 | 89.69 | 80.72 |
| Avg | 43.12 | 89.15 | 73.10 | 73.95 | 73.47 |
| Stdv | 10.86 | 4.35 | 10.74 | 10.90 | 6.59 |
| P value |  | 0.00049 | 0.015 | 0.013 | 0.006 |

Comparing Examples 4A and 4C, the cosmetic composition of Example 4C provided significantly superior average niacinamide penetration results with a combination of glycerin, hexyldecanol, and the diols propylene glycol and hexylene glycol as compared to Example 4A, which did not include hexyldecanol or glycerin but did include the diols butylene glycol and pentylene glycol. Example 4D which included glycerin, hexyldecanol, and the diols pentylene glycol and hexylene glycol and Example 4E which included glycerin, hexyldecanol, and the diols triethylene glycol and hexylene glycol also displayed superior average niacinamide penetration as compared to Example 4A. Interestingly, Example 4B which included glycerin, hexyldecanol, and a combination of the four diols butylene glycol, pentylene glycol, hexylene glycol, and hexanediol, provided significantly superior average niacinamide penetration results when compared to Example 4A. Interestingly, Example 4B with a ratio of diols/glycerin/hexyldecanol to niacinamide of 5:1 provided superior average niacinamide as compared to Examples 4C-4E which had a ratio of diols/glycerin/hexyldecanol to niacinamide of 3.3:1. This data suggests that it is possible to achieve superior (and/or more efficient) niacinamide penetration in the presence of glycerin by combining hexyldecanol with a combination of two or more diols such as propylene glycol, butylene glycol, triethylene glycol, pentylene glycol, hexylene glycol, and hexanediol. Table 7 also illustrates some of the many potential combinations of diols that can be included in cosmetic compositions also including glycerin, niacinamide, and hexyldecanol to achieve superior niacinamide penetration.

From Examples 2 and 3 and without intending to be bound by any theory, it appears that some overall qualitative observations may be made and/or inferred. First, the negative impact of glycerin on niacinamide penetration can be significantly reduced and/or obviated by adding an effective amount of hexyldecanol to a cosmetic composition. In addition, it appears that glycerin in the presence of hexyldecanol can in some instances increase, rather than decrease, niacinamide penetration. Second, generally increasing the ratio of diols/glycerin/hexydecanol to niacinamide can increase niacinamide penetration, and ratios greater than 2:1 may provide at least a doubling of niacinamide penetration and ratios greater than 3:1 may provide even better results. Third, combining two or more diols with hexyldecanol in the presence of glycerin may provide superior niacinamide penetration results compared to merely increasing the concentration of hexyldecanol. Fourth, it may be possible to achieve similar penetration results with lower concentrations of ingredients when combining two or more diols with hexyldecanol versus merely increasing the concentration of hexyldecanol. Fifth, it appears that at least some diols may be providing a different and/or complimentary penetration mechanism of action from hexyldecanol in view of: i) the observation that the addition of hexyldecanol can substantially increase average niacinamide penetration in the presence of glycerin versus the addition pentylene glycol, and ii) the observation that hexyldecanol and pentylene glycol had similar average niacinamide penetration values in the absence of glycerin but quite different individual penetration enhancement effects in the presence of glycerin.

In some embodiments, the cosmetic compositions may have a concentration of one or more liquid diols, by weight of the cosmetic composition, of greater than 1%, 2%, 3% 4%, 6%, 8%, 10%, 12%, 15%, or 20% and/or less than 30%, 25%, 20% or 15%. In some embodiments, the cosmetic compositions may have a concentration of one or more liquid diols, by weight of the cosmetic composition, of greater than about 1%, 2%, 3% 4%, 6%, 8%, 10%, 12%, 15%, or 20% and/or less than about 30%, 25%, 20% or 15%. In some embodiments, the total concentration of diols/glycerin/hexydecanol is greater than 10%, 11%, 12%, 13%, 14%, 16%, 18%, 20%, or 22% and/or less than 35%, 30%, 25%, or 20%. In some embodiments, the total concentration of diols/glycerin/hexydecanol is greater than about 10%, 11%, 12%, 13%, 14%, 16%, 18%, 20%, or 22% and/or less than about 35%, 30%, 25%, or 20%. In some embodiments, the ratio of the total concentration of diols/glycerin/hexyldecanol to niacinamide is at least 2:1, 3:1, 4:1, or 5:1. In some embodiments, the ratio of the total concentration of diols/glycerin/hexyldecanol to niacinamide is at least about 2:1, 3:1, 4:1, or 5:1. In some embodiments, the cosmetic compositions have a concentration of a vitamin B compound, by weight, of greater than 2%, 3%, 4%, or 5% and/or less than 10%, 8%, or 6%. In some embodiments, the cosmetic compositions have a concentration of a vitamin B compound, by weight, of greater than about 2%, 3%, 4%, or 5% and/or less than about 10%, 8%, or 6%. In some embodiments, the cosmetic composition has an average vitamin B total recovery, as a percentage of total dose using a Franz cell test method, greater than 50%, 60%, 70%, 80%, or 90% and/or less than 95%, 90%, 80%, or 70%. In some embodiments, the cosmetic composition has an average vitamin B total recovery, as a percentage of total dose using a Franz cell test method, greater than about 50%, 60%, 70%, 80%, or 90% and/or less than about 95%, 90%, 80%, or 70%.

V. OTHER INGREDIENTS

In addition to the previously described ingredients, the cosmetic compositions described herein may also comprise one or more optional ingredients. For example, the cosmetic composition may comprise from about 1% to about 95% by weight of water. The cosmetic composition may comprise from about 1% to about 95% by weight of one or more oils. The cosmetic composition may comprise from about 0.1%, 0.5%, 1%, 2%, 5%, 10%, 15%, 20%, 25%, 30%, 35%, 40%, 45%, 50%, 55%, 60%, 65%, 70%, 75%, 80%, 85%, or 90% to about 90%, 85%, 80%, 75%, 70%, 65%, 60%, 55%, 50%, 45%, 40%, 35%, 30%, 25%, 20%, 15%, 10%, 5%, or 3% of the one or more oils. Oils may be used to solubilize, disperse, or carry materials that are not suitable for water or water soluble solvents. Suitable oils include silicones, hydrocarbons, esters, amides, ethers, and mixtures thereof. Oils may be fluid at room temperature. The oils may be volatile or nonvolatile. "Non-volatile" means a material that exhibits a vapor pressure of no more than about 0.2 mm of mercury at 25° C. at one atmosphere and/or a material that has a boiling point at one atmosphere of at least about 300° C. "Volatile" means that the material exhibits a vapor pressure of at least about 0.2 mm. of mercury at 20° C. Volatile oils may be used to provide a lighter feel when a heavy, greasy film is undesirable. When the cosmetic composition is in the form of an emulsion, oils are carriers typically associated with the oil phase. The cosmetic composition can be in the form of a water-in-oil emulsion, an oil-in-water emulsion, or a water-in-silicone emulsion.

Suitable oils include volatile oils. In certain embodiments, the volatile oils may have a viscosity ranging from about 0.5 to 5 centistokes at 25° C. Volatile oils may be used to promote more rapid drying of the cosmetic composition after it is applied to skin. Nonvolatile oils are also suitable for use in the cosmetic composition. Nonvolatile oils are often used for emolliency and protective properties.

Suitable silicone oils include polysiloxanes. Polylsiloxanes may have a viscosity of from about 0.5 to about 1,000,000 centistokes at 25° C. Such polysiloxanes can be represented by the general chemical formula:

$$R_3SiO[R_2SiO]_xSiR_3$$

wherein R is independently selected from hydrogen or $C_{1-30}$ straight or branched chain, saturated or unsaturated alkyl, phenyl or aryl, trialkylsiloxy; and x is an integer from 0 to about 10,000, chosen to achieve the desired molecular weight. In certain embodiments, R is hydrogen, methyl, or ethyl. Commercially available polysiloxanes include the polydimethylsiloxanes, which are also known as dimethicones, examples of which include the DM-Fluid series from Shin-Etsu, the Vicasil® series sold by Momentive Performance Materials Inc., and the Dow Corning® 200 series sold by Dow Corning Corporation. Specific examples of suitable polydimethylsiloxanes include Dow Corning® 200 fluids (also sold as Xiameter® PMX-200 Silicone Fluids) having viscosities of 0.65, 1.5, 50, 100, 350, 10,000, 12,500 100,000, and 300,000 centistokes.

Suitable dimethicones include those represented by the chemical formula:

$$R_3SiO[R_2SiO]_x[RR'SiO]_ySiR_3$$

wherein R and R' are each independently hydrogen or $C_{1-30}$ straight or branched chain, saturated or unsaturated alkyl, aryl, or trialkylsiloxy; and x and y are each integers of 1 to 1,000,000 selected to achieve the desired molecular weight. Suitable silicones include phenyl dimethicone (Botansil™ PD-151 from Botanigenics, Inc.), diphenyl dimethicone (KF-53 and KF-54 from Shin-Etsu), phenyl trimethicone (556 Cosmetic Grade Fluid from Dow Corning), or trimethylsiloxyphenyl dimethicone (PDM-20, PDM-200, or PDM-1000 from Wacker-Belsil). Other examples include alkyl dimethicones wherein at least R' is a fatty alkyl (e.g., $C_{12-22}$). A suitable alkyl dimethicone is cetyl dimethicone, wherein R' is a straight C16 chain and R is methyl. Cetyl dimethicone, is available as 2502 Cosmetic Fluid from Dow Corning or as Abil Wax 9801 or 9814 from Evonik Goldschmidt GmbH.

Cyclic silicones are one type of silicone oil that may be used in the cosmetic composition. Such silicones have the general formula:

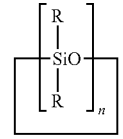

wherein R is independently selected from hydrogen or $C_{1-30}$ straight or branched chain, saturated or unsaturated alkyl, phenyl or aryl, trialkylsiloxy; and where n=3-8 and mixtures thereof. Commonly, a mixture of cyclomethicones is used where n is 4, 5, and/or 6. Commercially available cyclomethicones include Dow Corning UP-1001 Ultra Pure Fluid (i.e. n=4), Dow Corning XIAMETER® PMX-0245 (i.e. n=5), Dow Corning XIAMETER® PMX-0245 (i.e. n=6), Dow Corning 245 fluid (i.e. n=4 and 5), and Dow Corning 345 fluid (i.e. n=4, 5, and 6).

Suitable hydrocarbon oils include straight, branched, or cyclic alkanes and alkenes. The chain length may be selected based on desired functional characteristics such as volatility. Suitable volatile hydrocarbons may have between 5-20 carbon atoms or, alternately, between 8-16 carbon atoms.

Other suitable oils include esters. The suitable esters typically contained at least 10 carbon atoms. These esters include esters with hydrocarbyl chains derived from fatty acids or alcohols (e.g., mono-esters, polyhydric alcohol esters, and di- and tri-carboxylic acid esters). The hydrocarbyl radicals of the esters hereof may include or have covalently bonded thereto other compatible functionalities, such as amides and alkoxy moieties (e.g., ethoxy or ether linkages, etc.). Exemplary esters include, but are not limited to, isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, C12-15 alkyl benzoate, diisopropyl adipate, dibutyl adipate, and oleyl adipate. Other suitable esters are further described in the Personal Care Product Council's *International Cosmetic Ingredient Dictionary and Handbook*, Thirteenth Edition, 2010, under the functional category of "Esters." Other esters suitable for use in the cosmetic composition include those known as polyhydric alcohol esters and glycerides.

Other suitable oils include amides. Amides include compounds having an amide functional group while being liquid at 25° C. and insoluble in water. Suitable amides include N-acetyl-N-butylaminopropionate, isopropyl N-lauroylsarcosinate, and N,N,-diethyltoluamide. Other suitable amides are disclosed in U.S. Pat. No. 6,872,401.

Other suitable oils include ethers. Suitable ethers include saturated and unsaturated fatty ethers of a polyhydric alcohol, and alkoxylated derivatives thereof. Exemplary ethers include $C_{4-20}$ alkyl ethers of polypropylene glycols, and di-$C_{8-30}$ alkyl ethers. Suitable examples of these materials include PPG-14 butyl ether, PPG-15 stearyl ether, dioctyl ether, dodecyl octyl ether, and mixtures thereof.

The cosmetic composition may comprise an emulsifier. An emulsifier is particularly suitable when the cosmetic composition is in the form of an emulsion or if immiscible materials are being combined. The cosmetic composition may comprise from about 0.05%, 0.1%, 0.2%, 0.3%, 0.5%, or 1% to about 20%, 10%, 5%, 3%, 2%, or 1% emulsifier. Emulsifiers may be nonionic, anionic, or cationic. Non-limiting examples of emulsifiers are disclosed in U.S. Pat. Nos. 3,755,560, 4,421,769, and McCutcheon's, *Emulsifiers and Detergents*, 2010 Annual Ed., published by M. C. Publishing Co. Other suitable emulsifiers are further described in the Personal Care Product Council's *International Cosmetic Ingredient Dictionary and Handbook*, Thirteenth Edition, 2006, under the functional category of "Surfactants—Emulsifying Agents."

Suitable emulsifiers include the following classes of ethers and esters: ethers of polyglycols and of fatty alcohols, esters of polyglycols and of fatty acids, ethers of polyglycols and of fatty alcohols which are glycosylated, esters of polyglycols and of fatty acids which are glycosylated, ethers of $C_{12-30}$ alcohols and of glycerol or of polyglycerol, esters of $C_{12-30}$ fatty acids and of glycerol or of polyglycerol, ethers of oxyalkylene-modified $C_{12-30}$ alcohols and of glycerol or polyglycerol, ethers of $C_{12-30}$ fatty alcohols comprising and of sucrose or of glucose, esters of sucrose and of $C_{12-30}$ fatty acids, esters of pentaerythritol and of $C_{12-30}$ fatty acids, esters of sorbitol and/or of sorbitan and of $C_{12-30}$ fatty acids, ethers of sorbitol and/or of sorbitan and of alkoxylated sorbitan, ethers of polyglycols and of cholesterol, esters of $C_{12-30}$ fatty acids and of alkoxylated ethers of sorbitol and/or sorbitan, and combinations thereof.

Linear or branched type silicone emulsifiers may also be used. Particularly useful polyether modified silicones include KF-6011, KF-6012, KF-6013, KF-6015, KF-6015, KF-6017, KF-6043, KF-6028, and KF-6038 from Shin Etsu. Also particularly useful are the polyglycerolated linear or branched siloxane emulsifiers including KF-6100, KF-6104, and KF-6105 from Shin Etsu.

Emulsifiers also include emulsifying silicone elastomers. Suitable emulsifying silicone elastomers may include at least one polyalkyl ether or polyglycerolated unit. Polyoxyalylenated emulsifying silicone elastomers that may be used include those sold by Shin-Etsu Silicones under the names KSG-21, KSG-20, KSG-30, KSG-31, KSG-32, KSG-33; KSG-210 (dimethicone/PEG-10/15 crosspolymer dispersed in dimethicone); KSG-310 (PEG-15 lauryl dimethicone crosspolymer); KSG-320 (PEG-15 lauryl dimethicone crosspolymer dispersed in isododecane); KSG-330 (PEG-15 lauryl dimethicone crosspolymer dispersed in triethylhexanoin), KSG-340 (PEG-10 lauryl dimethicone crosspolymer and PEG-15 lauryl dimethicone crosspolymer). Other silicone emulsifying elastomers are supplied by Dow Corning™, including PEG-12 dimethicone crosspolymers (DC 9010 and 9011). Other suitable silicone emulsifiers sold by Dow Corning include DC9010 and DC9011. Polyglycerolated emulsifying silicone elastomers are disclosed in PCT/WO 2004/024798. Such elastomers include Shin-Etsu's KSG series, such as KSG-710 (dimethicone/polyglycerin-3 crosspolymer dispersed in dimethicone); or lauryl dimethicone/polyglycerin-3 crosspolymer dispersed in a variety of solvent such as isododecane, dimethicone, triethylhexanoin, available as KSG-810, KSG-820, KSG-830, or KSG-840 from Shin-Etsu.

Structuring agents may be used to increase viscosity, thicken, solidify, or provide solid or crystalline structure to the cosmetic composition. Structuring agents are typically grouped based on solubility, dispersibility, or phase compatibility. Examples of aqueous or water structuring agents include polymeric agents, natural or synthetic gums, polysaccharides, and the like. For example, the cosmetic composition may comprises from about 0.0001%, 0.001%, 0.01%, 0.05%, 0.1%, 0.5%, 1%, 2%, 3%, 5% to about 25%, 20%, 10%, 7%, 5%, 4%, or 2%, by weight of the cosmetic composition, of one or more structuring agents.

Polysaccharides and gums may be suitable aqueous phase thickening agents. Suitable classes of polymeric structuring agents include but are not limited to carboxylic acid polymers, polyacrylamide polymers, sulfonated polymers, high molecular weight polyalkylglycols or polyglycerins, copolymers thereof, hydrophobically modified derivatives thereof, and mixtures thereof.

Examples of oil structuring agents include silicone and organic based materials. Suitable ranges of oil structuring agents are from about 0.01%, 0.05%, 0.1% 0.5%, 1%, 2.5%, 5%, or 10% to about 30%, 25%, 20%, 15%, 10%, or 5%. Suitable oil phase structuring agents may be silicone based, such as silicone elastomers, silicone gums, silicone waxes, linear silicones having a degree of polymerization allowing the silicone to increase the viscosity of the oil phase. Examples of silicone structuring agents include, but are not limited to, silicone elastomers, silicone gums, and silicone waxes, Suitable silicone elastomers may be in the powder form, or dispersed or solubilized in solvents such as volatile or nonvolatile silicones, or silicone compatible vehicles such as paraffinic hydrocarbons or esters. Examples of silicone elastomer powders include vinyl dimethicone/methicone silsesquioxane crosspolymers like KSP-100, KSP-101, KSP-102, KSP-103, KSP-104, KSP-105, available from Shin-Etsu, hybrid silicone powders that contain a fluoroalkyl group like KSP-200, available from Shin-Etsu, which is a fluoro-silicone elastomer, and hybrid silicone powders that contain a phenyl group such as KSP-300, available from Shin-Etsu, which is a phenyl substituted silicone elastomer; and DC 9506 available from Dow Corning.

Examples of silicone elastomer dispersions include dimethicone/vinyl dimethicone crosspolymers supplied by a variety of suppliers including Dow Corning Corporation under the tradenames DC9040 or DC9041, Momentive under the tradename SFE 839, or Shin-Etsu Silicones under the tradenames KSG-15, 16, 18. KSG-15 has the INCI name cyclopentasiloxane (and) dimethicone/vinyl dimethicone crosspolymer. KSG-18 has the INCI name diphenylsiloxy phenyl trimethicone (and) dimethicone/phenyl vinyl dimethicone crosspolymer. Silicone elastomers may also be purchased from Grant Industries under the Gransil trademark. Other suitable silicone elastomers have long chain alkyl substitutions such as lauryl dimethicone/vinyl dimethicone crosspolymers supplied by Shin Etsu under the tradenames KSG-41, KSG-42, KSG-43, and KSG-44, wherein the elastomer is dispersed in solvents including mineral oil, isodocane, triethylhexanoin, or squalene, respectively. Other suitable silicone elastomers may have polyglycerine substitutions such as lauryl dimethicone/polyglycerin-3 crosspolymers supplied by Shin Etsu under the tradenames KS G-810, KS G-820, KS G-830, and KS G-840, wherein the elastomer is dispersed in solvents including mineral oil, isodocane, triethylhexanoin, or squalene, respectively. Other suitable silicone elastomers may have polyglycol substitutions such as PEG-15/lauryl dimethiconecrosspolymers supplied by Shin Etsu under the tradenames KSG-310, KSG-320, KSG-330, and KSG-340, wherein the elastomer is dispersed in solvents including mineral oil, isodocane, triethylhexanoin, or squalene, respectively. Other suitable silicone elastomers having polyglycol substitutions include Shin Etsu's KSG-210, a dimethicone/PEG-10/15 crosspolymer in dimethicone.

Silicone gums are another oil phase structuring agent. The silicone gum typically has a viscosity ranging from about 500,000 to 100 million cst at 25° C., from about 600,000 to 20 million, from about 600,000 to 12 million cst. Suitable silicone gums include those sold by Wacker-Belsil under the trade names CM3092, Wacker-Belsil 1000, or Wacker-Belsil DM 3096. A particularly suitable silicone gum is as dimethiconol, available from Dow Corning Corporation under the trade name 1-1254 Fluid, 2-9023 Fluid, and 2-9026 Fluid. Dimethiconol is often sold as a mixture with a volatile or nonvolatile silicone such as Dow Corning 1401 Fluid, 1403 Fluid, and 1501 Fluid.

Another type of oily phase structuring agent includes silicone waxes. Silicone waxes may be referred to as alkyl silicone waxes and can be semi-solids or solids at room temperature. The term "alkyl silicone wax" means a polydimethylsiloxane having a substituted long chain alkyl (such as C16 to 30) that confers a semi-solid or solid property to the siloxane. Examples of such silicone waxes include stearyl dimethicone, which may be purchased from Evonik Goldschmidt GmbH under the tradename Abil Wax 9800 or from Dow Corning under the tradename 2503. Another example is bis-stearyl dimethicone (which may be purchased from Gransil Industries under the tradename Gransil A-18), behenyl dimethicone, or behenoxy dimethicone.

Other suitable viscosity increasing agents include polyamides and polysilicone-polyamide copolymers. Suitable polysilicone-polyamide copolymers are disclosed in U.S. Patent Application Publication No. 2004/0170586.

Other oil phase structuring agents may be one or more natural or synthetic waxes such as animal, vegetable, or mineral waxes. Suitable silicone waxes are disclosed in U.S. Pat. Nos. 5,413,781 and 5,725,845, and further include alkylmethyl polysiloxanes, C10-C60 alkyl dimethicones, and mixtures thereof.

Other structuring agents include natural or synthetic montmorillonite minerals, silicas, silicates, silica silylate, and alkali metal or alkaline earth metal derivatives thereof.

The cosmetic compositions may optionally contain a UV active. As used herein, "UV active" includes both sunscreen agents and physical sunblocks. Suitable UV actives may be organic or inorganic. Suitable UV actives are listed in the functional category of "Sunscreen Agents" in the Personal Care Product Council's *International Cosmetic Ingredient Dictionary and Handbook*, Thirteenth Edition, 2010. Suitable UV actives include those defined or proposed by regulatory agencies in the US (e.g., 21 CFR part 352, 68 Federal Register 41386, 70 Federal Register 72449, or 71 Federal Register 42405), Europe (Regulation No 1223/2009 of the EU Parliament; Annex VI), Japan, China, Australia, New Zealand, or Canada. For example, the cosmetic composition may comprise from about 0.01% to about 20%, by weight of the cosmetic composition, of a UV active. The cosmetic composition may also comprise a sufficient amout of UV active to yield a Sun Protection Factor of at least about 15, 30 45, or 50. SPF testing is conventional and well understood in the art. A suitable SPF test is prescribed in 21 C.F.R. 352, Subpart D.

Suitable UV actives include dibenzoylmethane derivatives including 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxy dibenzoylmethane, 4-tert-butyl-4'-methoxy dibenzoylmethane (i.e., butyl methoxydibenzoylmethane or avobenzone) (commercially available as PARSOL® 1789 from DSM), 2-methyl-5-isopropyl-4'-methoxy dibenzoylmethane, 2-methyl-5-tert-butyl-4'-methoxydibenzoylmethane, 2,4-dimethyl-4'-methoxy dibenzoylmethane, and 2,6-dimethyl-4-tert-butyl-4'-methoxy dibenzoylmethane. Other suitable UV actives include 2-ethylhexyl-p-methoxycinnamate (commercially available as PARSOL® MCX from DSM), 2-hydroxy-4-methoxybenzophenone, benzonphenone-3 (i.e. oxybeznone), octyldimethyl-p-aminobenzoic acid, digalloyltrioleate, 2,2-dihydroxy-4-methoxybenzophenone, ethyl-4-(bis(hydroxy-propyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene, zinc oxide, titanium dioxide, and mixtures thereof.

Particularly suitable UV actives are 2-ethylhexyl-p-methoxycinnamate, 4-tert-butyl-4'-methoxy dibenzoylmethane, 2-hydroxy-4-methoxybenzo-phenone, 2-phenylbenzimidazole-5-sulfonic acid, octocrylene, zinc oxide, titanium dioxide, and mixtures thereof.

Other suitable UV actives include 4-methylbenzylidene camphor (commercially available as PARSOL® 5000 from DSM or Eusolex 6300 from Merck), methylene bis-benzotriazolyl tetramethylbutylphenol (i.e., bisoctrizole, commercially available as Tinosorb® M from BASF), bis-ethylhexyloxyphenol methoxyphenol triazine (i.e., bemotrizinol, commercially available as Tinosorb® S from BASF), disodium phenyl dibenzimidazole tetrasulfonate (i.e., Bisdisulizole disodium, commercially available as Neo Heliopan® AP from Symrise), Ethylhexyl triazone (commercially available as Uvinul® T 150 from BASF), Drometrizole trisiloxane (marketed as Mexoryl XL by L'Oreal), Sodium Dihydroxy Dimethoxy Disulfobenzophenone (i.e., benzophenone-9, commercially available as Uvinul® DS 49 from BASF), Diethylamino Hydroxybenzoyl Hexyl Benzoate (commercially available as Uvinul® A Plus from BASF), diethylhexyl butamido triazone (i.e., Iscotrizinol, commercially available as Uvasorb® HEB by 3V Sigma), Polysilicone-15 (i.e., commercially available as PARSOL® SLX from DSM), and Isoamyl p-Methoxycinnamate (i.e., amiloxate, commercially available as Neo Heliopan® E 1000 from Symrise).

The cosmetic compositions may be generally prepared by conventional methods such as those known in the art of making cosmetic compositions. Such methods typically involve mixing of ingredients in one or more steps to a relatively uniform state, with or without heating, cooling, application of vacuum, and the like. Typically, emulsions are prepared by first mixing the aqueous phase materials separately from the fatty phase materials and then combining the two phases as appropriate to yield the desired continuous phase. The cosmetic compositions are preferably prepared such as to optimize stability (physical stability, chemical stability, photostability, etc.) and/or delivery of active materials. The cosmetic composition may be provided in a package sized to store a sufficient amount of the cosmetic composition for a treatment period. The size, shape, and design of the package may vary widely. Certain package examples are described in U.S. Pat. Nos. D 570,707; D391, 162; D516,436; D535,191; D542,660; D547,193; D547, 661; D558,591; D563,221; 2009/0017080; 2007/0205226; and 2007/0040306.

VI. METHODS OF USE

The cosmetic compositions disclosed herein may be applied to one or more skin surfaces as part of a user's daily routine. Additionally or alternatively, the cosmetic compositions herein may be used on an "as needed" basis. For example, the cosmetic composition may be applied to a facial skin care surface in need of treatment by the cosmetic composition. The facial skin surface may include one or more of the cheek, forehead, and peri-orbital areas of the face. In some examples, one or more of these skin surfaces may be identified as needing treatment and one or more of these skins surfaces may be treated with the cosmetic composition. For example, the cosmetic composition can also be applied to the facial skin surface at least once per day, twice per day, or three times per day for a period of 7, 14, 21, or 28 days or more. In another example, the cosmetic composition may be applied to a different skin surface or applied to facial skin and one or more different skin surfaces.

VII. EXAMPLES

The following examples are given solely for the purpose of illustration and are not to be construed as limiting the invention, as many variations thereof are possible.

Example 1

Niacinamide/Glycerin Measurements

In vitro skin penetration studies were conducted to characterize the impact of glycerin upon in vitro skin penetration of radiolabeled niacinamide in several cosmetic compositions. The kinetics of in vitro radiolabeled niacinamide skin penetration were determined at a fixed glycerin concentration, and the impact of glycerin and niacinamide product concentrations upon the skin penetration of radiolabeled niacinamide and glycerin over six hours were measured. Table 9 provides a general description of the four cosmetic composition types that were tested. It should be noted that the individual products used in the studies may have varied somewhat in specific concentrations from the general values in Table 8. Also, composition #1 was repeated in two different studies with varying concentrations of niacinamide and glycerin.

TABLE 8

General descriptions of the chassis used in the in vitro skin permeation experiments

| Chassis | Composition #1 | Composition #2 | Composition #3 | Composition #4 |
|---|---|---|---|---|
| Type | O/W Emulsion | W/Si Emulsion | W/Si Emulsion | Water Gel |
| Water | 72.3 | 65.7 | 48.8 | ~78 |
| Polyols | | 2.0 | 3.0 | 3.2 |
| Silicone | 2.0 | 12.8 | 34.7 | 1.5 |
| Oil | 5.0 | | | 1.5 |
| Emulsifiers | Nonionic Surfactant Acrylic Copolymers Fatty Alcohols | Silicone Elastomers | Silicone Elastomers | Nonionic Acrylic Copolymers |

Split thickness cadaver skin was obtained from AlloSource (Englewood, Colo.). Tritiated water was from PerkinElmer (Boston, Mass.) while $^{14}C$ niacinamide was obtained from American Radiochemicals (St. Louis, Mo.). For all studies, split-thickness human cadaver skin was maintained at −70° C. until thawed at ambient conditions, rinsed with distilled water, cut into appropriately sized sections, and mounted in standard Franz-type diffusion cells (0.79 cm$^2$) which were placed in heating/stirring blocks thermostatted to maintain a skin surface temperature of about 34° C. The receptors [~5 mL] were filled with a solution of 1% polysorbate 20 (VWR International, West Chester, Pa.) in Dulbecco's Phosphate Buffered Saline [PBS] (Sigma-Aldrich, Inc., St. Louis, Mo.) with agitation provided by magnetic stir bars, and the skin allowed to equilibrate for at least two hours.

Six cells were randomized to each treatment in a given study based upon $^3H_2O$ flux through the mounted skin. 150 µL $^3H_2O$ were applied to the mounted cadaver skin for five minutes and any non-absorbed liquid subsequently removed with a cotton swab. After a minimum of one hour to achieve equilibrium, the receptor contents were collected. Liquid scintillation cocktail, LCS, (14 mL) was added to the contents of each receptor and also to triplicate 150 µL aliquots of $^3H_2O$. The LSC solutions and appropriate blanks were assayed for total radiolabel by liquid scintillation counting for one minute using a pre-set quench curve. Blank corrected DPM (disintegrations per minute) in each receptor was converted to µL $^3H_2O$ using the mean of the blank corrected DPM of the 150 µL aliquots of $^3H_2O$, and water flux for each cell was calculated as the quotient of the $^3H_2O$ volume detected in the receptor and the available skin surface area. Fresh receptor fluid was then added to the receptor portions of the Franz cells and the cells allowed to further equilibrate overnight.

Following the overnight equilibration period, the receptor compartments were filled with fresh media. Except as noted below, approximately 5 µL of product with radiotracer were applied to the individual cells using a positive displacement pipette. The receptor solution was collected and replaced at 2 and 4 hr with a final collection at 6 hr. At the end of the test time (s), each skin sample was wiped two times with Whatman filter paper soaked with PBS containing 1% polysorbate 20 and once with filter paper soaked with 70%/30% ethanol/distilled water to remove unabsorbed (residual) product. The epidermis (including stratum corneum) was separated from the residual dermis by dissection.

Disintegrations-per-minute (DPM) obtained for the various components of each cell (all receptor collections, filter paper wipes, epidermis, and dermis) were blank corrected and summed to obtain a total recovered radiolabel value for a given cell. This value was then compared with the specific radiolabel activity of the product (DPM/theoretical dose) to estimate the percent recovery of the theoretical dose.

The blank corrected DPM of each compartment were then normalized to the total recovered radiolabel value to obtain a "percent recovered radiolabel" parameter for each component. This compensates for variations in the amount of product dosed due to its viscosity and improves study precision.

Cumulative receptor amounts were calculated as the sums of the various receptor collections to a given time point. A total skin value was calculated as the sum of the epidermis and dermis fractions, and a total permeated value calculated as the sum of total skin and total cumulative receptor.

For those studies which incorporated test products with varying concentrations of the permeant being investigated (e.g. niacinamide), the percent recovered values were subsequently converted to "fraction radiolabel recovered" by dividing by 100, and then to amount (µg–equivalents (µg-eq) permeant by multiplying by the target dose (5 mg) and fraction permeant in the test product.

The data from this series of studies, summarized in FIG. 1, suggest that the addition of glycerin decreases niacinamide skin penetration and that increasing the glycerin concentration further decreases niacinamide skin penetration from a variety of cosmetic compositions.

Example 2

Niacinamide/Glycerin/Hexyldecanol Measurements

The cosmetic compositions set forth in Table 8 were prepared.

TABLE 9

| Phase | Component | 2A | 2B | 2C | 2D | 2E | 2F | 2G | 2H |
|---|---|---|---|---|---|---|---|---|---|
| A | Water | QS | QS | QS | QS | QS | QS | QS | QS |
|   | Acrylates/C10-30 Alkyl Acrylate Crosspolymer | 0.4 | 0.4 | 0.4 | 0.4 | 0.4 | 0.4 | 0.4 | 0.4 |
| B | Glycerin |  | 7 |  | 7 |  |  | 7 | 7 |
|   | Niacinamide | 5 | 5 | 5 | 5 | 5 | 5 | 5 | 5 |
| C | Triethanolamine | 0.5 | 0.5 | 0.5 | 0.5 | 0.5 | 0.5 | 0.5 | 0.5 |
| D | Polyoxyethylene (20) sorbitan monolaurate |  |  | 0.5 | 0.5 | 1 | 1.5 | 1 | 1.5 |
| E | 2-Hexyl-1-decanol |  |  | 5 | 5 | 10 | 15 | 10 | 15 |
| F | DMDM Hydantoin Iodopropynyl Butylcarbamate | 0.3 | 0.3 | 0.3 | 0.3 | 0.3 | 0.3 | 0.3 | 0.3 |

Components of Phase A were mixed together with stiffing using a suitable mixer (e.g., Tekmar model RW20DZM) and blade while warming to approximately 50 C. Mixing continued until visually all crosspolymer is well dispersed. Components of Phase B are added to Phase A with continual mixing and Phase A was allowed to cool to room temperature. Phase C is added to Phase A/B with continual stirring. If necessary, components of Phase D and E are added followed by milling of product at approximately 8000 rpm for 5 minutes using a Tekmar T-25 mill. Phase F is added with to Phase A-E and mixed using a suitable mixer for approx. 5 minutes.

Next, human cadaver skin samples were mounted in standard Franz-type diffusion cells (0.79 cm$^2$ surface area) maintained at about 37° C. Six replicates for each compositional leg were prepared. The receptor compartments were filled with 5 mL phosphate buffered saline (PBS—pH 7.4) that included 1% polysorbate-20 and 0.02% sodium azide, and the skin allowed to equilibrate for two hours. The cells were randomized to treatment group based upon $^3H_2O$ flux through the mounted skin (150 µL of $^3H_2O$ applied for five minutes, removed and followed by collection of receptor fluid after 60 minutes). Diffusion cells were randomized by ranking each cell according to water flux and distributing cells across treatment legs such that each group included cells across the range of observed water flux. Each treatment group typically had 6 replicates.

Aliquots of the test products/formulations set forth in Table 8 were spiked with $^{14}C$-niacinamide with approximately 3 µCi per 300 mg product aliquot, mixed and assayed for total radioactivity in triplicate using Ultima Gold (available from Perkin-Elmer) liquid scintillation cocktail (LSC) and liquid scintillation counting (Tri-Carb 2500 TR Liquid Scintillation Analyzer, PerkinElmer, Boston, Mass.). The skin samples were topically dosed with 5 µL of the radiolabeled niacinamide composition using a positive displacement pipette. The cosmetic composition was gently spread over the surface of the skin samples (0.79 cm$^2$) using the pipet tip. The receptor solution was collected and replaced at 6 hours following application with a final collection at 24 hrs. After the final receptor collection, each skin sample was wiped two times with Whatman filter paper soaked with PBS/Tween 20 and once with 70%/30% ethanol/water to remove unabsorbed (residual) product. The epidermis was separated from the residual dermis by dissection. The skin sections were dissolved in 0.50-1.25 mL Soluene-350 (Perkin Elmer, Boston, Mass.) at 60° C. overnight, and all receptor collections, filter paper wipes, and solubilized tissue sections were counted using liquid scintillation counting. Disintegrations-per-minute (DPM) for each compartment of each cell were blank corrected and summed to obtain a total recovered radiolabel value for a given cell. The DPM of each compartment were then normalized to the total recovered radiolabel value to obtain a "percent recovered radiolabel" parameter for each compartment (individual receptor collections, epidermis, dermis, and wipes for mass balance). Cumulative receptor values to each collection time point were calculated as the sum of the individual collections to that time point, with the total receptor value as the sum of all individual collections. The total recovered percentage value was the sum of the epidermis (including stratum corneum) and dermis values, and the total permeated value the sum of total skin and cumulative receptor values. Tables 1, 2, and 3 summarize the total percentage values of radiolabeled niacinamide recovered.

Example 3

Niacinamide/Glycerin/Hexyldecanol/Diol Measurements

The cosmetic compositions set forth in Table 10 were prepared in the same manner as previously described with respect to Example 2.

TABLE 10

|  | 3A | 3B | 3C | 3D | 3E | 3F | 3G | 3H | 3I |
|---|---|---|---|---|---|---|---|---|---|
| Water | QS | QS | QS | QS | QS | QS | QS | QS | QS |
| Acrylates/C10-30 Alkyl Acrylate Crosspolymer | 0.4 | 0.4 | 0.4 | 0.4 | 0.4 | 0.4 | 0.4 | 0.4 | 0.4 |
| Glycerin | 7 | 7 | 7 | 7 |  |  |  |  | 7 |
| 1,2-Pentanediol | 6 |  | 6 | 6 | 6 |  |  |  | 6 |
| Hexylene Glycol |  |  |  |  |  |  |  | 1 |  |
| 1,2-Hexanediol |  | 1 | 1 |  |  | 1 |  |  | 1 |
| Niacinamide | 5 | 5 | 5 | 5 | 5 | 5 | 5 | 5 | 5 |
| Triethanolamine | 0.5 | 0.5 | 0.5 | 0.5 | 0.5 | 0.5 | 0.5 | 0.5 | 0.5 |
| Polyoxyethylene (20) sorbitan monolaurate | 0.5 | 0.5 | 0.5 |  |  |  |  |  | 1 |
| 2-Hexyl-1-decanol | 5 | 5 | 5 |  |  |  |  |  | 10 |
| DMDM Hydantoin Iodopropynyl Butylcarbamate | 0.3 | 0.3 | 0.3 | 0.3 | 0.3 | 0.3 | 0.3 | 0.3 | 0.3 |

Using generally the same test procedures as set forth in Example 2, DPM for each compartment of each cell were blank corrected and summed to obtain a total recovered radiolabel value for a given cell. The DPM of each compartment were then normalized to the total recovered radiolabel value to obtain a "percent recovered radiolabel" parameter for each compartment (individual receptor collections, epidermis, dermis, and wipes for mass balance). Cumulative receptor values to each collection time point were calculated as the sum of the individual collections to that time point, with the total receptor value as the sum of all individual collections. The total percentage recovered value was the sum of the epidermis (including stratum corneum) and dermis values, and the total permeated value the sum of total skin and cumulative receptor values. Tables 4, 5, and 6 summarize the total percentage values of radiolabeled niacinamide recovered for Examples 3A to 3H. Example 3I, however, produced an average total niacinamide recovery of 69.43 (std=13.45, p-value=0.004), which is less than Example 3C and less than would have been expected. It is not clear whether this result is an anomaly or perhaps related to detection limits of the instrumentation.

Example 4

Niacinamide/Glycerin/Hexyldecanol/Diol Measurements

The cosmetic compositions set forth in Table 11 were prepared in the same manner as previously described with respect to Example 2.

TABLE 11

|  | 4A | 4B | 4C | 4D | 4E |
|---|---|---|---|---|---|
| Water | QS | QS | QS | QS | QS |
| Glycerin |  | 7 | 7 | 7 | 7 |
| Propylene glycol |  |  | 3 |  |  |
| Butylene glycol | 2 | 3 |  |  |  |
| Triethylene glycol |  |  |  |  | 3 |
| Pentylene glycol | 3 | 6 |  | 3 |  |
| Hexylene glycol |  | 3 | 1.5 | 1.5 | 1.5 |
| Hexanediol |  | 1 |  |  |  |
| Benzyl alcohol | 0.2 | 0.2 | 0.2 | 0.2 | 0.2 |
| Phenoxyethanol | 0.25 | 0.25 | 0.25 | 0.25 | 0.25 |
| Eldew |  |  | 2 | 2 | 2 |
| Dibutyl adipate |  |  | 1 | 1 | 1 |
| 2-Hexyl-1-decanol |  | 5 | 5 | 5 | 5 |
| Isopropyl myristate |  |  | 1 | 1 | 1 |
| Oleic acid |  | 1 | 1 | 1 | 1 |
| Isostearic acid |  |  |  |  |  |
| Vitamin E acetate |  | 1 | 0.5 | 0.5 | 0.5 |
| Niacinamide | 5 | 5 | 5 | 5 | 5 |

Using generally the same test procedures as set forth in Example 2, DPM for each compartment of each cell were blank corrected and summed to obtain a total recovered radiolabel value for a given cell. The DPM of each compartment were then normalized to the total recovered radiolabel value to obtain a "percent recovered radiolabel" parameter for each compartment (individual receptor collections, epidermis, dermis, and wipes for mass balance). Cumulative receptor values to each collection time point were calculated as the sum of the individual collections to that time point, with the total receptor value as the sum of all individual collections. The total percentage recovered value was the sum of the epidermis (including stratum corneum) and dermis values, and the total permeated value the sum of total skin and cumulative receptor values. Tables 7 summarize the total percentage values of radiolabeled niacinamide recovered for Examples 4A-4E.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cosmetic composition suitable for topical application, comprising:
    i) Glycerin at a concentration of from about 5% to about 25% by weight of the cosmetic composition;
    ii) hexanediol and one or more materials selected from the group consisting of pentylene glycol, hexylene glycol, propylene glycol, triethylene glycol, and butylene glycol;

iii) hexyldecanol; and iv) niacinamide;

wherein the ratio of the combination of i) and ii) and iii) to iv) is about 2:1 to about 5:1; wherein the niacinamide has a concentration from about 5% to about 10% by weight of the cosmetic composition.

2. The cosmetic composition of claim 1, wherein the ratio of the combination of i) and ii) and iii) to iv) is about 3:1 to about 3.8:1.

3. The cosmetic composition of claim 1, wherein the cosmetic composition is provided in the form selected from the group consisting of a water-in-oil emulsion, an oil-in-water emulsion, or a water-in-silicone emulsion.

4. A cosmetic composition according to claim 1 wherein the ratio of the A combination of i) and ii) and iii) to iv) in the cosmetic composition is about 2:1 to about 4.4:1.

5. The cosmetic composition of claim 4, wherein the glycerin has a concentration from about 10% to about 25% by weight of the cosmetic composition.

6. The cosmetic composition of claim 4, wherein the cosmetic composition is provided in the form of a water-in-oil emulsion, an oil-in-water emulsion, or a water-in-silicone emulsion.

7. A cosmetic composition suitable for topical application, comprising:
   i) from about 5% to about 25% by weight of the composition of glycerin;
   ii) 1,6-hexanediol;
   iii) hexyldecanol; and
   iv) niacinamide;
   wherein the ratio of the combination of i) and ii) and iii) to iv) is about 2:1 to about 5:1; wherein the niacinamide has a concentration from about 5% to about 10% by weight of the cosmetic composition.

* * * * *